US011002642B2

(12) United States Patent
Oshinski et al.

(10) Patent No.: US 11,002,642 B2
(45) Date of Patent: May 11, 2021

(54) DEMARCATION TEMPLATE FOR HAZARDOUS CONTAMINANT TESTING

(71) Applicant: Becton, Dickinson and Company, Franklin Lakes, NJ (US)

(72) Inventors: Matthew Oshinski, Oak Ridge, NJ (US); Austin Jason Mckinnon, Herriman, UT (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 156 days.

(21) Appl. No.: 16/133,985

(22) Filed: Sep. 18, 2018

(65) Prior Publication Data

US 2019/0086295 A1     Mar. 21, 2019

Related U.S. Application Data

(60) Provisional application No. 62/561,557, filed on Sep. 21, 2017.

(51) Int. Cl.
    *G01N 1/02*          (2006.01)
    *G01N 33/15*        (2006.01)
    (Continued)

(52) U.S. Cl.
CPC ................ *G01N 1/02* (2013.01); *B01L 9/56* (2019.08); *G01N 33/15* (2013.01); *B01L 3/5023* (2013.01);
(Continued)

(58) Field of Classification Search
CPC .... G01N 1/02; G01N 33/15; G01N 2001/028; G01N 1/38; G01N 2001/027; B01L 9/56; B01L 3/5023; B01L 3/5029
(Continued)

(56) References Cited

U.S. PATENT DOCUMENTS

| 1,853,238 A | 4/1932 | Shields |
| D229,689 S | 12/1973 | Dragotta |

(Continued)

FOREIGN PATENT DOCUMENTS

| WO | WO 1995/25948 | 9/1995 |
| WO | WO 2010/001296 | 1/2010 |

(Continued)

OTHER PUBLICATIONS

Chemoglo, LLC, "ChemoGlo™—Detecting and Removing Hazardous Drugs"; available for download at https://web.archive.org/web/20150801115335/http://chemoglo.com/ at least as early as Aug. 1, 2015; 1 page.

(Continued)

*Primary Examiner* — Robert R Raevis
(74) *Attorney, Agent, or Firm* — Knobbe, Martens, Olson & Bear LLP

(57) ABSTRACT

Aspects of the disclosure relate to demarcation templates for demarcating a test area on a test surface and for providing visual guidance to a user to precisely and accurately swab the test surface in order to determine the presence and/or concentration of an analyte of interest on the test surface. In one aspect, the analyte of interest is a hazardous contaminant. Some templates can include alignment markings around the border demarcating the test area to provide such guidance to users, and can include graphical use instructions on a removable central portion of the template. The template can be adhesive to be securely fixed to the test surface for accurate demarcation of the test area throughout sampling.

23 Claims, 12 Drawing Sheets

(51) Int. Cl.
  *B01L 9/00* (2006.01)
  *G01N 1/38* (2006.01)
  *B01L 3/00* (2006.01)
(52) U.S. Cl.
  CPC .............. *B01L 3/5029* (2013.01); *G01N 1/38* (2013.01); *G01N 2001/028* (2013.01)
(58) Field of Classification Search
  USPC ............................ 73/864.71, 863; 600/572
  See application file for complete search history.

(56) References Cited

U.S. PATENT DOCUMENTS

| | | | |
|---|---|---|---|
| 3,841,973 A * | 10/1974 | Wilkins et al. | .......... G01N 1/04 73/864.31 |
| 4,278,437 A | 7/1981 | Haggar | |
| 4,724,307 A | 2/1988 | Dutton et al. | |
| 4,956,302 A | 9/1990 | Gordon et al. | |
| 5,373,748 A | 12/1994 | Lioy et al. | |
| 5,422,273 A | 6/1995 | Garrison et al. | |
| 5,511,654 A | 4/1996 | de la Rocha | |
| 5,511,934 A | 4/1996 | Bracchi et al. | |
| D383,851 S | 9/1997 | Wong | |
| 5,798,273 A | 8/1998 | Shuler et al. | |
| 5,823,592 A * | 10/1998 | Kalidindi | ................. G01N 1/02 294/24 |
| D425,625 S | 5/2000 | Niermann | |
| D438,979 S | 2/2001 | Gomes et al. | |
| 6,382,036 B1 * | 5/2002 | Woodmansee | .......... G01N 1/02 73/864.71 |
| 6,924,153 B1 | 8/2005 | Boehringer et al. | |
| D520,643 S | 5/2006 | Clarke et al. | |
| 7,114,403 B2 | 10/2006 | Wu et al. | |
| D558,357 S | 12/2007 | Byrd et al. | |
| D559,397 S | 1/2008 | Eriksson et al. | |
| D560,281 S | 1/2008 | Kozak et al. | |
| D574,507 S | 8/2008 | Muir et al. | |
| D594,131 S | 6/2009 | Nguyen | |
| D640,795 S | 6/2011 | Jackson et al. | |
| 8,128,871 B2 | 3/2012 | Petruno et al. | |
| 8,486,717 B2 | 7/2013 | O'Farrell et al. | |
| D743,046 S | 11/2015 | Poll et al. | |
| D743,571 S | 11/2015 | Jackson et al. | |
| 9,488,585 B2 | 11/2016 | Emeric et al. | |
| 2002/0035869 A1 * | 3/2002 | Schroder | ................... B08B 1/00 73/432.1 |
| 2004/0018634 A1 | 1/2004 | Hajizadeh et al. | |
| 2004/0248106 A1 | 12/2004 | Leonard et al. | |
| 2005/0084842 A1 | 4/2005 | O'Connor | |
| 2005/0106753 A1 | 5/2005 | Wu et al. | |
| 2005/0136540 A1 | 6/2005 | Quine et al. | |
| 2005/0136553 A1 | 6/2005 | Kaylor et al. | |
| 2005/0181517 A1 | 8/2005 | Chandler et al. | |
| 2005/0250141 A1 | 11/2005 | Lambert et al. | |
| 2007/0276786 A1 | 11/2007 | Piedmonte | |
| 2008/0118397 A1 | 5/2008 | Slowey et al. | |
| 2009/0015273 A1 | 1/2009 | Gossen et al. | |
| 2009/0223635 A1 | 9/2009 | Lawless | |
| 2010/0077843 A1 | 4/2010 | Doraisamy et al. | |
| 2011/0117025 A1 | 5/2011 | Dacosta et al. | |
| 2011/0201099 A1 | 8/2011 | Anderson et al. | |
| 2012/0011944 A1 * | 1/2012 | Maughan | ................ A61B 10/02 73/864.34 |
| 2012/0107956 A1 | 5/2012 | Boehringer et al. | |
| 2012/0264229 A1 | 10/2012 | Wan | |
| 2012/0282154 A1 | 11/2012 | Slowey et al. | |
| 2013/0280143 A1 | 10/2013 | Zucchelli et al. | |
| 2014/0017812 A1 | 1/2014 | Smith et al. | |
| 2014/0080129 A1 | 3/2014 | Klunder et al. | |
| 2014/0121487 A1 | 5/2014 | Faybishenko et al. | |
| 2014/0183256 A1 | 7/2014 | Calio et al. | |
| 2014/0210857 A1 | 7/2014 | Liu et al. | |
| 2014/0309556 A1 | 10/2014 | Fletcher et al. | |
| 2015/0132795 A1 | 5/2015 | Griswold et al. | |
| 2015/0302662 A1 | 10/2015 | Miller | |
| 2016/0019716 A1 | 1/2016 | Huang et al. | |
| 2016/0041167 A1 | 2/2016 | Campbell et al. | |
| 2016/0077013 A1 | 3/2016 | Attar et al. | |
| 2016/0078680 A1 | 3/2016 | Reif et al. | |
| 2016/0258874 A1 | 9/2016 | Truex | |
| 2017/0016045 A1 | 1/2017 | McDaniel | |
| 2017/0153185 A1 | 6/2017 | Kisner et al. | |
| 2017/0154438 A1 | 6/2017 | Kisner et al. | |
| 2018/0247024 A1 | 8/2018 | Divine et al. | |
| 2018/0293350 A1 | 10/2018 | Dimov et al. | |
| 2019/0035153 A1 | 1/2019 | Dange | |
| 2019/0086296 A1 | 3/2019 | West | |
| 2019/0086305 A1 | 3/2019 | Harding et al. | |
| 2019/0086380 A1 | 3/2019 | Harding et al. | |
| 2019/0086431 A1 | 3/2019 | Isaacson et al. | |
| 2019/0088026 A1 | 3/2019 | Isaacson et al. | |
| 2019/0120727 A1 | 4/2019 | Harding et al. | |
| 2020/0241020 A1 | 7/2020 | Oshinski | |

FOREIGN PATENT DOCUMENTS

| | | |
|---|---|---|
| WO | WO 2011/095599 | 8/2011 |
| WO | WO 2016/090176 | 6/2016 |

OTHER PUBLICATIONS

Chemoglo, LLC, ChemoGlo™ User Manual; available for download at https://web.archive.org/web/20150801115335/http://chemoglo.com/ at least as early as Aug. 1, 2015; 11 pages.

International Search Report and Written Opinion dated Dec. 6, 2018 for Int'l App. No. PCT/US2018/051440.

Becton Dickinson—Veritor™ System—For Rapid Detection of Respiratory Syncytial Virus (RSV), Aug. 2017, Retrieved from the internet: <URL: https://www.bd.com/en-us/offerings/capabilities/microbiology-solutions/point-of-care-testing/veritor-system> in 16 pages.

Becton Dickinson—BD Diagnostics Preanalytical Systems—Product Catalogue 2014-15; 2013, Retrieved from internet: <URL:https://www.bd.com/be/dutch/pdfs/PAS_BNL_Prod_Cat_2014_2015_LR_Full_Catalog ue.pdf> in 31 pages.

Technical Service Consultants Ltd., TS/15-T Product Specification Sheet; Issue #5 of Jun. 6, 2016; Retrieved from the Internet: URL: <http://www.tscswabs.co.uk/uploads/images/product-pdfs/product_specification/spec_TS15-T.pdf> in 20 pages.

Becton Dickinson—BD HD Check Analyzer—Nursing Brochure; Mar. 2018, in 8 pages.

Becton Dickinson—BD HD Check Analyzer—Pharmacy Brochure; Mar. 2018, in 6 pages.

Preprocess, Inc., Sampling and Analytical Technique Considerations for Microbial Surface Swab Testing. 2015; Retrieved from the internet: <URL:http://www.preprocessinc.com/files/documents/d5840edf837f077be7b12e53494ed5b8.pdf> in 3 pages.

* cited by examiner

DEMARCATION TEMPLATE FOR HAZARDOUS CONTAMINANT TESTING

CROSS-REFERENCE TO RELATED APPLICATIONS

This application claims the benefit of U.S. Provisional Patent Application No. 62/561,557, filed on Sep. 21, 2017, entitled "DEMARCATION TEMPLATE FOR HAZARDOUS CONTAMINANT TESTING," the contents of which are hereby incorporated by reference herein.

TECHNICAL FIELD

Systems and methods disclosed herein are directed to environmental contaminant testing, and, more particularly, to templates that guide users to accurately sample a test area.

BACKGROUND

Antineoplastic drugs are used to treat cancer, and are most often found in a small molecule (like fluoruracil) or antibody format (like Rituximab). Detection of antineoplastic drugs is critical for determining if there is contamination or leakage where the drugs are used and/or dispensed, such as hospital and pharmacy areas.

The nature of antineoplastic drugs make them harmful to healthy cells and tissues as well as the cancerous cells. Precautions should be taken to eliminate or reduce occupational exposure to antineoplastic drugs for healthcare workers. Pharmacists who prepare these drugs and nurses who may prepare and administer them are the two occupational groups who have the highest potential exposure to antineoplastic agents. Additionally, physicians and operating room personnel may also be exposed through the treatment of patients, as patients treated with antineoplastic drugs can excrete these drugs. Hospital staff, such as shipping and receiving personnel, custodial workers, laundry workers and waste handlers, all have the potential to be exposed to these drugs during the course of their work. The increased use of antineoplastic agents in veterinary oncology also puts these workers at risk for exposure to these drugs.

SUMMARY

Antineoplastic drugs are antiproliferative. In some cases they affect the process of cell division by damaging DNA and initiating apoptosis, a form of programmed cell death. While this can be desirable for preventing development and spread of neoplastic (e.g., cancerous) cells, antineoplastic drugs can also affect rapidly dividing non-cancerous cells. As such, antineoplastic drugs can suppress healthy biological functions including bone marrow growth, healing, hair growth, and fertility, to name a few examples.

Studies have associated workplace exposures to antineoplastic drugs with health effects such as skin rashes, hair loss, infertility (temporary and permanent), effects on reproduction and the developing fetus in pregnant women, increased genotoxic effects (e.g., destructive effects on genetic material that can cause mutations), hearing impairment and cancer. These health risks are influenced by the extent of the exposure and the potency and toxicity of the hazardous drug. Although the potential therapeutic benefits of hazardous drugs may outweigh the risks of such side effects for ill patients, exposed health care workers risk these same side effects with no therapeutic benefit. Further, it is known that exposures to even very small concentrations of antineoplastic drugs may be hazardous for workers who handle them or work near them, and for known carcinogenic agents there is no safe level of exposure.

Environmental sampling can be used to determine the level of workplace contamination by antineoplastic agents. Sampling and decontamination of contaminated areas is complicated, however, by a lack of quick, inexpensive methods to first identify these areas and then determine the level of success of the decontamination. Although analytical methods are available for testing for the presence of antineoplastic drugs in environmental samples, these methods require shipment to outside labs, delaying the receipt of sampling results.

In one example sampling system suitable for use with the devices of the present disclosure, work surfaces can be tested for the presence of antineoplastic agents in an environment. Results of the test can be provided very quickly, at the site of testing, so that the operator of the test, other personnel in the area, and/or remote systems can be alerted to the presence and/or concentration of antineoplastic agents very close in time to the test event, in some cases within 1-2 minutes. Methods of testing include providing the surface with a buffer solution and wiping the wetted surface with an absorbent swab, or by wiping the surface with a swab pre-wetted with the buffer solution. The buffer fluid can have properties that assist in picking up contaminants from the surface. In some implementations, the buffer fluid can have properties that assist in releasing collected contaminants from swab material. The collected contaminants can be mixed into a homogeneous solution for testing. The buffer solution, together with any collected contaminants, can be expressed or extracted from the swab to form a liquid sample. This liquid sample can be analyzed for presence and/or quantity of specific antineoplastic agents. For example, the solution can be provided onto an assay (such as but not limited to a lateral flow assay) which is read by an assay reader device to identify presence and/or a concentration of the contaminant in the liquid sample.

The accuracy of testing for the presence and/or concentration of a contaminant in a fluid sample is highly dependent on various test factors. Test results can provide a measurement in the form of concentration of contaminant in a tested environment, for example contaminant mass per square unit area. Accordingly, precision and accuracy in measuring the sampled area can be an important factor to obtain an accurate test result. Accurately measuring a specific sample area can involve demarcating a test area of the surface to be tested and then sampling the entire demarked area. Existing sampling systems require the test operator to measure out test area dimensions and place physical markers, such as adhesive dots, to define a rectangular test area. The test operator of such existing systems is then responsible for ensuring that the entire area is swabbed before cleaning up the markers. This approach has a number of drawbacks including requiring a lengthy setup, being subject to measurement and marker placement errors, and increasing the risk of exposure of the test operator to potential hazardous drug contamination through placement and removal of the markers.

These and other problems are addressed in embodiments of the hazardous drug collection and detection systems described herein, which include templates having a removable instructions portion with graphical sampling instructions, and a border forming an open area configured to demarcate a test area with the removable instructions portion removed. The template can also include an adhesive layer for securing it to a test surface. The present technology provides improved accuracy for identifying antineoplastic drug concentrations, including trace amounts of antineoplastic drugs, compared to existing systems. The disclosed templates can enable more accurate sampling from the tested area, for example by the consistent demarcation of a pre-specified area. A detection system is capable of accurately detecting quantities of even trace amounts of antineoplastic agents based on the known sampled area and of providing results quickly (including immediately after collection). Advantageously, testing and detection can occur at the location of the collection so that immediate, quantitative assessment of contamination level can be determined without the delay required for laboratory sample processing.

Accordingly, one aspect relates to a system for guiding collection of a hazardous contaminant sample, comprising a handle configured for collection of the hazardous contaminant sample from a test surface; and a template including a border having an outer perimeter and an inner perimeter with edges of the inner perimeter defining an open area configured to demarcate a test area for the collection of the hazardous contaminant sample, and a plurality of alignment markings provided along at least one of the edges of the inner perimeter, the plurality of alignment markings provided at a spacing selected to provide visual guidance to a user for wiping the entire test area with the handle.

In some embodiments of the system, the border is formed from a substrate, wherein the plurality of alignment markings are printed on a first surface of the substrate, the template further comprising an adhesive provided on a second surface of the substrate opposing the first surface. Some further embodiments comprise a protective backing layer removably provided to cover the adhesive prior to use. Some further embodiments comprise a removable portion of the template secured to the protective backing layer within the open area of the border. In some further embodiments, the substrate comprises the removable portion, the removable portion further comprising at least one graphical instruction for guiding the user through the collection of the hazardous contaminant sample printed on the first surface. In some further embodiments, the substrate comprises the removable portion, the system further comprising a separation line extending through the substrate and separating the border and the removable portion.

Some embodiments of the system further comprise a reader device configured to determine a test result based on the hazardous contaminant sample collected from the test surface within the test area demarcated by the template. In some further embodiments, the border comprises a machine-readable pattern identifying the surface area of the test area, wherein the reader device includes a scanning device, at least one computer-readable memory having stored thereon executable instructions, and one or more processors in communication with the at least one computer-readable memory and configured to execute the instructions to cause the reader device to cause the scanning device to capture data representing the machine-readable pattern, and determine the surface area of the test area based on analyzing the data.

Another aspect relates to a system for guiding collection of a hazardous contaminant sample, comprising a template including a border having an outer perimeter and an inner perimeter with edges of the inner perimeter defining an open area configured to demarcate a test area for the collection of the hazardous contaminant sample; and a reader device configured to receive an indication of a surface area of the test area of the template, and to determine a test result based on the hazardous contaminant sample from the test surface and on the surface area of the test area of the template.

In some embodiments of the system, the border comprises a plurality of alignment markings provided along at least one of the edges of the inner perimeter, the plurality of alignment markings provided at a spacing selected to provide visual guidance to a user for wiping the entire test area. In some further embodiments, the border is formed from a substrate, and wherein the plurality of alignment markings are printed on a first surface of the substrate, the template further comprising an adhesive provided on a second surface of the substrate opposing the first surface. Some further embodiments comprise a protective backing layer removably provided to cover the adhesive prior to use. Some further embodiments comprise a removable portion of the template secured to the protective backing layer within the open area of the border. In some further embodiments, the substrate comprises the removable portion, the removable portion further comprising at least one graphical instruction for guiding the user through the collection of the hazardous contaminant sample printed on the first surface. In some further embodiments, the substrate comprises the removable portion, the system further comprising a separation line extending through the substrate and separating the border and the removable portion.

In some embodiments of the system, one surface of the template is provided with an adhesive, the template further comprising a protective backing layer removably provided to cover the adhesive prior to use.

Another aspect relates to a template for guiding collection of a hazardous contaminant sample from a surface, comprising a substrate comprising a border having an outer perimeter and an inner perimeter with edges of the inner perimeter defining an open area configured to demarcate a test area on the surface for the collection of the hazardous contaminant sample, a separation line provided as one or more cuts through the substrate along the inner perimeter, and a removable portion provided within the inner perimeter; an adhesive provided on a surface of the substrate configured to secure at least the border to the surface; and a protective backing layer removably provided to cover the adhesive prior to use.

In some embodiments of the template, the adhesive secures the border and the removable portion to the protective backing layer prior to use. In some embodiments of the template, the border comprises a plurality of alignment markings provided at a spacing selected to provide visual guidance to a user for wiping the entire test area. In some embodiments of the template, the removable portion comprises at least one graphical instruction for guiding a user through the collection of the hazardous contaminant sample. In some embodiments of the template, the removable portion is configured to be removed from the border prior to the collection of the hazardous contaminant sample.

Another aspect relates to a method for applying a template for guiding collection of a hazardous contaminant sample to a surface, comprising obtaining a template as described herein; peeling the border away from the protective backing layer at a first corner of the border; securing the first corner of the border to the surface using an exposed portion of the adhesive; folding the protective backing layer away from the first corner and under a portion of the border that is unsecured to the surface; peeling the protective backing layer away from the first corner to progressively expose more of the adhesive; securing additional portions of the border to the surface using corresponding portions of the adhesive as it is progressively exposed; and upon fully removing the protective backing layer from the border, securing a second corner of the border to the surface, the second corner diagonally opposing the first corner.

Another aspect relates to a method for applying a template for guiding collection of a hazardous contaminant sample to a surface, comprising obtaining a template as described herein; completely removing the border from the protective backing layer; securing a first edge of the border to the surface using a portion of the adhesive provided on the first edge; progressively securing portions of second and third edges of the border onto the surface using corresponding portions of the adhesive provided on the portions of the second and third edges, the second and third edges extending from the first edge; and securing a fourth edge of the border to the surface using a portion of the adhesive provided on the fourth edge, the fourth edge opposing the first edge and connecting the second and third edges.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

Figure 1A:
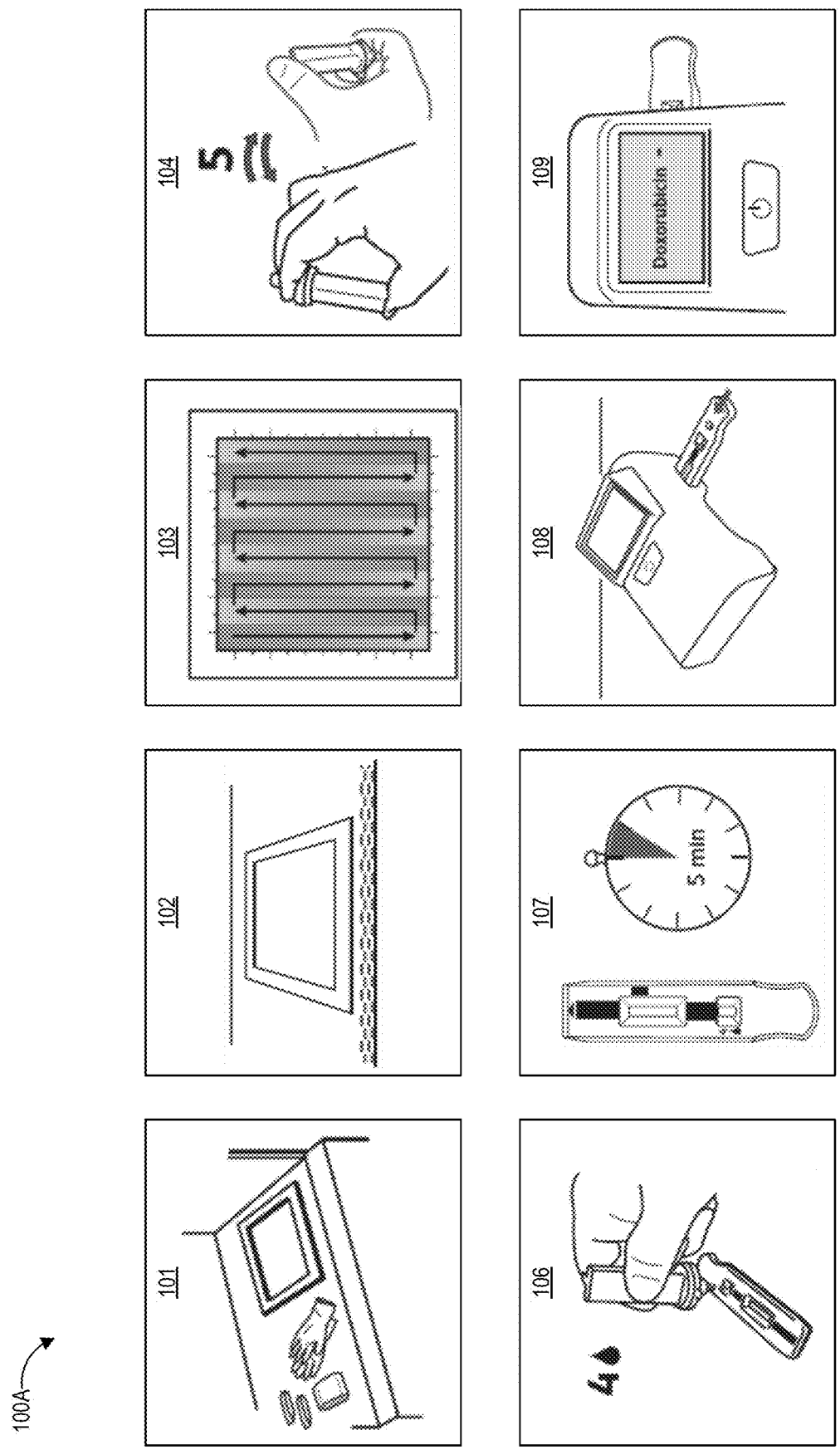
FIGS. 1A-1D graphically illustrate steps of an example method of collecting and testing a liquid sample as described herein.

Embodiments of the disclosure relate to systems and techniques for detection of hazardous environmental contaminants, such as but not limited to antineoplastic drugs used in the treatment of cancer, with increased sensitivity to trace concentrations of antineoplastic drugs in collected samples. A kit for such testing can include a collection system and a testing device, and the collection system can include a template for demarcating the test area. The template can have an adhesive backing, a border defining an open area for demarcating the test area, and a portion that is separable from the border to create the open area providing use instructions to a user. The border can include markings that assist a user in performing sampling in a regular, precise, constrained way that thoroughly contacts all or substantially all of the test surface exposed within the open area of the template. Throughout this disclosure, example systems, kits, and methods will be described with reference to collection, testing, and detection of antineoplastic agents, but it will be understood that the present technology can be used to collect, test, and detect any particle, molecule, or analyte of interest.

A precise method of demarcating and sampling from a specified area can be important in order to obtain an accurate test result in the form of drug mass per square unit area (e.g., nanograms per square centimeter). For example, a sample can be collected from a test surface by using a buffer liquid to wet the surface and using a swab to absorb the buffer liquid and any particles of hazardous drug contamination. Alternatively, any particles of hazardous drug contamination can be collected by wiping the surface with a swab pre-wetted with the buffer solution. When the sample is tested, a test device may be able to identify the concentration of the hazardous drug in the volume of the liquid sample. In order to convert this measurement into a measurement of drug concentration on the test surface, some implementations can use the following formula:

$$\alpha = (C v_b)/(A \eta_p \eta_e)$$

where $\alpha$ represents the contamination surface density (e.g., ng/cm$^2$), C represents the concentration of the sample in the liquid sample, $v_b$ represents the fluid volume of the buffer solution used to collect the sample, A represents the surface area swabbed, $\eta_p$ represents the pick-up efficiency of the swab material and buffer solution, and $\eta_e$ represents the extraction efficiency of contaminant picked up by the swab material. The goal is to have a high concentration signal with low variability, however noise (e.g., variation) in these variables can cause the test to generate either false positive or false negative results. The disclosed templates provide guidance for reducing the variation in the surface area swabbed, leading to heightened accuracy in sample testing, and in particular to a more accurate contamination surface density measurement.

Embodiments of the systems and methods described herein can advantageously determine two important aspects regarding contamination of a tested surface quickly and with high precision. First, the disclosed systems and methods can determine the presence of even a very small amount of a hazardous contaminant. This provides an important benefit over manual sampling (e.g., sampling performed without the disclosed templates), because if there are just a few molecules on the surface, the user may miss the molecules entirely if they do not sample the test area in a regular, constrained, precise way. This type of sampling can lead to a false negative, leading to a missed opportunity to fix a leak or breach of protocol. In one example, the false negative reading may lead to healthcare workers continuing work in the tested area, resulting in their exposure to the hazardous contaminant. The disclosed templates can aid users in reliably sampling specific demarcated areas. Embodiments of the physical templates described herein can ensure the user is reliably informed of the presence of even small amounts of hazardous agent, for example by guiding the user to perform a thorough sampling such that the results provided by test devices are more accurate than results based on other sampling methods.

Second, the disclosed systems and methods can be used to more precisely determine the concentration of a detected hazardous contaminant by providing an accurate metric regarding actual sampled area. This is important because the presence of a very small or trace concentrations of certain hazardous drugs may be tolerable or even expected within an environment in some scenarios, but the difference between a smaller, acceptable trace concentration and a larger, unacceptable and potentially dangerous trace concentration may be very small (e.g., on the order of nanograms per centimeter squared). The disclosed templates, together with test systems and methods described herein, enable the user to now know very quickly and reliably if the concentration of a hazardous contaminant has elevated to dangerous conditions.

Although the templates, test systems, and methods described herein are typically described herein with reference to test strips and lateral flow assay reader devices, it will be appreciated that the described templates can be implemented in any detection system that seeks to detect the presence of and/or quantify any particle, molecule, or analyte of interest. The test devices described herein are not limited to lateral flow assay test strips, nor to test strips generally. Any suitable test device can be used with implementations of the templates described herein. Features described herein can be implemented in reader devices that analyze other types of assays, such as but not limited to molecular assays, and provide a test result. Further, the collected fluid can be transferred to a centrifuge, spectrometer, chemical assay, or other suitable test device to determine the presence and/or concentration of the target particle, molecule, or analyte of interest, including but not limited to hazardous substances. Additionally, although templates described herein are described as being applied to horizontal and vertical surfaces in some non-limiting examples, the templates are not limited to application to planar surfaces. Templates described herein can be used to test, for example, non-planar surfaces such as but not limited to IV poles, curved desk or door handles, and other fixtures that are commonly present in the test environment and that may be contaminated with even a minute amount of a hazardous substance.

Drugs successfully treat many types of illnesses and injuries, but virtually all drugs have side effects associated with their use. Not all adverse side effects classify as hazardous, however. In the present disclosure, the term "hazardous drugs" is used according to the meaning adopted by the American Society of Health-System Pharmacists (ASHP), which refers to a drug as hazardous if studies in animals or humans have indicated that exposures to them have any one of four characteristics: genotoxicity; carcinogenicity; teratogenicity or fertility impairment; and serious organ damage or other toxic manifestation at low doses in experimental animals or treated patients.

Although described in the example context of ascertaining the presence and/or concentration of hazardous drugs such as antineoplastic agents, it will be appreciated that the disclosed devices and techniques for demarcating a test sampling area and guiding user sampling procedures can be used to detect the presence and/or concentration of any analyte of interest. An analyte can include, for example, drugs (both hazardous and non-hazardous), antibodies, proteins, haptens, nucleic acids and amplicons.

Various embodiments will be described below in conjunction with the drawings for purposes of illustration. It should be appreciated that many other implementations of the disclosed concepts are possible, and various advantages can be achieved with the disclosed implementations.

Overview of Example Sampling Method

FIGS. 1A-1D graphically illustrate steps of an example method of collecting and testing a liquid sample that can be performed using a template as described herein. FIG. 1A illustrates example steps of a testing method 100A for testing for the presence of an analyte on a test surface. One, some, or all of the depicted blocks of FIG. 1A can be printed as graphical user interface instructions on a template (either the border or the portion separable from the border to create the open area for sampling), the packaging of an assay and/or collection kit, or can be presented on a display screen of an assay reader device, a test area terminal, or a personal computing device of the user.

At block 101, the user can identify a sample location and gather a collection kit, assay cartridges, and a template. The collection kit can include a swab attached to a handle and a collection container. In some examples, the swab is pre-wetted with buffer solution and packaged together with the handle in a first sealed pouch and the collection container is packaged in a second sealed pouch. The assay cartridge may include an assay device housed inside a cartridge having a window or port aligned with a sample receiving zone of the assay device. In one implementation, the assay device is a test strip, for example but not limited to a lateral flow assay test strip. Also at block 101 the user can put on clean gloves prior to each sample collection and/or opening of the collection kit, both to protect the user from potential contamination on the surface and to protect the collected sample from contamination with anything on the user's hands.

At block 102, the user can establish a test area on the test surface. For example, the user can place a template over the intended location to clearly demarcate the area that will be swabbed. As described herein, block 102 can involve a user removing a central portion of the template to create an open area within a border, peeling the border away from an adhesive backing, and carefully placing the adhesive border on the test surface to ensure that the edges demarcating the open area are positioned straight and flat on the test surface. Also at block 102 the user can open the collection kit packaging, including opening the separately-packaged swab and handle.

At block 103, the user can swab the test area using slow and firm strokes. As shown, the user can methodically pass the swab in straight lines along the height of the test area all the way across the width of the test area. The template border can include markings that assist the user in maintaining even separation between adjacent swab stroke lines across the test surface. Such markings may be spaced apart by a distance determined based on a known width of a swab handle provided with the template, such that maintaining alignment of the swab handle with the markings causes the entire test area to be sampled. In some embodiments, the swab handle can additionally have markings, for example at the center point along its width, to further assist the sampling user with maintaining alignment between the swab handle and the template markings.

The test area may be one square foot in some embodiments, for example demarcated as a 12 inches by 12 inches (144 square inches) region. Other examples can use greater or smaller areas for collection including 10 inches by 10 inches, 8 inches by 8 inches, 6 inches by 6 inches and 4 inches by 4 inches, non-square rectangular regions (e.g., a 9 inches by 16 inches rectangle), and non-rectangular regions (e.g. circles). Different-sized templates may be specified for usage with different test surfaces. The particular template used can be indicated to a reader device, for example via a manual user input or via a barcode or other identifying pattern on the template scanned by the reader device. For example, a template providing a swab area of a 12 inches by 12 inches region can be indicated for use in sampling a countertop, while a smaller template demarcating a smaller swab area can be indicated for swabbing an IV pole. The reader device can adjust its test result calculations to account for the actual area tested, as indicated by the particular template used for the sampling procedure.

At block 104, the user can insert the swab into the collection container. In some examples, the collection container includes a t-shaped well. Though not illustrated, the swab may have a t-shaped cross-section that substantially matches that of the container well. The user seals the container with a top that includes a dripper cap, and fully inverts (e.g., turn upside down and then return to right-side-up) the sealed container five times. During these inversions, the liquid in the well of the container washes primarily over the swab material due to the cross-sectional shape of the well, and the handle slides within the well due to the well having a greater height than the handle. The inversion combined with the geometries of the container and handle and the flow of the buffer solution can extract collected contaminants from the swab material.

At block 106, the user can leave the swab and handle inside the container, remove the dripper cap, and squeeze (or allow gravity to draw) four drops into the sample well on each assay cartridge. For example, in some embodiments the user may drop sample onto multiple assays each designed to test for a different drug. In some examples anywhere between three and ten drops can produce suitable results on the assay. A drop is an approximated unit of measure of volume corresponding to the amount of liquid dispensed as one drop from a dropper or drip chamber via gravitational pull (sometimes aided by a positive pressure created within the container holding the liquid). Though the precise volume of any given drop depends upon factors such as the surface tension of the liquid of the drop, the strength of the gravitational field pulling on the drop, and the device and technique used to produce the drop, it is commonly considered to be a volume of 0.05 mL. In alternate embodiments the user may mechanically couple a fluid transfer portion of the collection device to a fluid transfer portion of the assay device to release a controlled volume of sample through a closed fluid pathway.

At block 107, the user can use a timer to allow the sample to develop for a period of time. For example, the sample can develop for about one minute, about two minutes, about three minutes, about four minutes, about five minutes, about six minutes, or some other amount of time. Other development times are possible. In some embodiments the timer can be built in to the programming of the reader device that reads the assay. The development time can vary depending on the particular test that is being performed and the particular operating parameters of the assay device.

At block 108, the user can insert the assay cartridge into an assay reader device. The assay cartridge can be inserted into the ready device prior to or after the sample is developed, depending upon the operational mode of the device. In some embodiments, the user may sequentially insert multiple cartridges for testing different aspects of the sample or for ensuring repeatability of test results.

At block 109, the assay reader device reads portions of the inserted cartridge (including, for example, detecting optical signals from exposed areas of a capture zone of a test strip housed in the cartridge), analyzes the signals to determine optical changes to test zone location(s) and optionally control zone location(s), determines a result based on the optical changes, and displays the result to the user. The device can optionally store the result or transmit the result over a network to a centralized data repository. As illustrated, the device displays a negative result for the presence of Doxorubicin in the sample. In other embodiments the device can display a specific detected concentration level in the sample and/or determined for the test area, and optionally can display confidence values in the determined result.

Embodiments of the reader devices described herein can determine the presence or the absence of a hazardous drug on a tested surface with a high degree of confidence, and display an indication of this test result to a user very quickly (in some instances, within 1 to 2 minutes) after the user tests the surface. In some cases, the reader device can determine a concentration of contamination and display an indication of the determined concentration to the user very quickly (in some instances, within 1 to 2 minutes) after the user tests the surface. In still further examples, the reader device correlates a detected level of contamination with a risk of human uptake and/or risk of harmful exposure to humans. To illustrate in one non-limiting example, an unintended human uptake of 1.0 ng/cm$^2$ of Cyclophosphamide, a hazardous antineoplastic drug, can be deemed a harmful exposure and/or exposure to a carcinogen. It will be understood that a different level of contamination of Cyclophosphamide could be established as a threshold for harmful exposure, and that the level of contamination for various antineoplastic drugs can be set to different levels depending on the needs of the user and the testing environment.

In this example, the reader device is configured to detect a level of contamination of Cyclophosphamide for a 12 inch by 12 inch (just as an example) sampled area that is $\frac{1}{10}^{th}$ of this 1.0 ng/cm$^2$ threshold level of Cyclophosphamide contamination, or 0.1 ng/cm$^2$. For example, the dynamic range of the assay test device (and reader devices described herein that read the disclosed assay devices) can be capable of detecting a level of contamination of Cyclophosphamide as low as about 0.1 ng/cm$^2$ per 12 inch by 12 inch sample test area. In one non-limiting embodiment, the reader device is configured to display an indication of an actual measured concentration of Cyclophosphamide. For example, a display on the reader device may display the reading "0.085 ng/cm$^2$" to the user upon completion of reading the test device. In another non-limiting embodiment, the reader device is configured to indicate a binary result to the user based on an actual measured concentration of Cyclophosphamide. For example, a display on the reader device may display the reading "−" or "−Cyclophosphamide" to the user upon completion of reading the test device when the actual measured concentration of Cyclophosphamide is less than about 0.1 ng/cm$^2$ (equivalent to a 93 ng mass of Cyclophosphamide for a 12 inch by 12 inch test sample area). The display on the reader device may display the reading "+" or "+Cyclophosphamide" to the user upon completion of reading the test device when the actual measured concentration of Cyclophosphamide is about 0.1 ng/cm$^2$ or greater (equivalent to a 93 ng mass of Cyclophosphamide for a 12 inch by 12 inch test sample area).

In some examples, the reader device is configured to correlate an actual measurement of contamination with a risk of human uptake and/or risk of harmful exposure to humans and to display an indication of the risk to the user upon completion of reading the test device. For instance, the reader device may be configured to correlate an actual measured concentration of Cyclophosphamide of less than about 0.1 ng/cm$^2$ as a reading within a window of acceptable error and/or with a low risk of harmful exposure. In this case, the reader device can display a reading of "No further action" to the user. The reader device can be configured to correlate an actual measured concentration of Cyclophosphamide of about 0.1 ng/cm$^2$ (equivalent to a 93 ng mass of Cyclophosphamide for a 12 inch by 12 inch test sample area) with a moderate risk of harmful exposure. In this case, the reader device can display a reading of "Notify others; Begin Decontamination" to the user. The reader device can be configured to correlate an actual measured concentration of Cyclophosphamide of greater than about 0.1 ng/cm$^2$ (equivalent to a 93 ng mass of Cyclophosphamide for a 12 inch by 12 inch test sample area) as a reading within a window of unacceptably high contamination. In this case, the reader device can display a reading of "Evacuate immediately" to the user. The reader device may also automatically transmit a warning or alert to the user with a warning sound or light (for example, a voice prompt or bright flashing light); transmit a warning or alert to other personnel within a distance of the reader device and the tested surface (for example, initiate voice prompts to evacuate the immediate area, emit a high-decibel siren, etc.); and/or transmit a warning or alert to personnel within or outside the physical location where the test event occurred (transmit, via a wired or wireless connection, an emergency notification to a head pharmacist, nurse, manager, safety officer, or regulatory agency that includes location of the test event, hazardous drug name, and the measured concentration of the hazardous drug). These examples are not intended to be limiting and it will be understood that other concentrations, thresholds, display readings, and warnings can be implemented in the systems described herein.

After testing the user can re-seal the container with a dripper cap and dispose of the collection device and assay (for example in compliance with hazardous waste regulations). Optionally, the user can execute any needed decontamination procedures, re-test a decontaminated surface, and perform required reporting of the result.

Figure 1B:
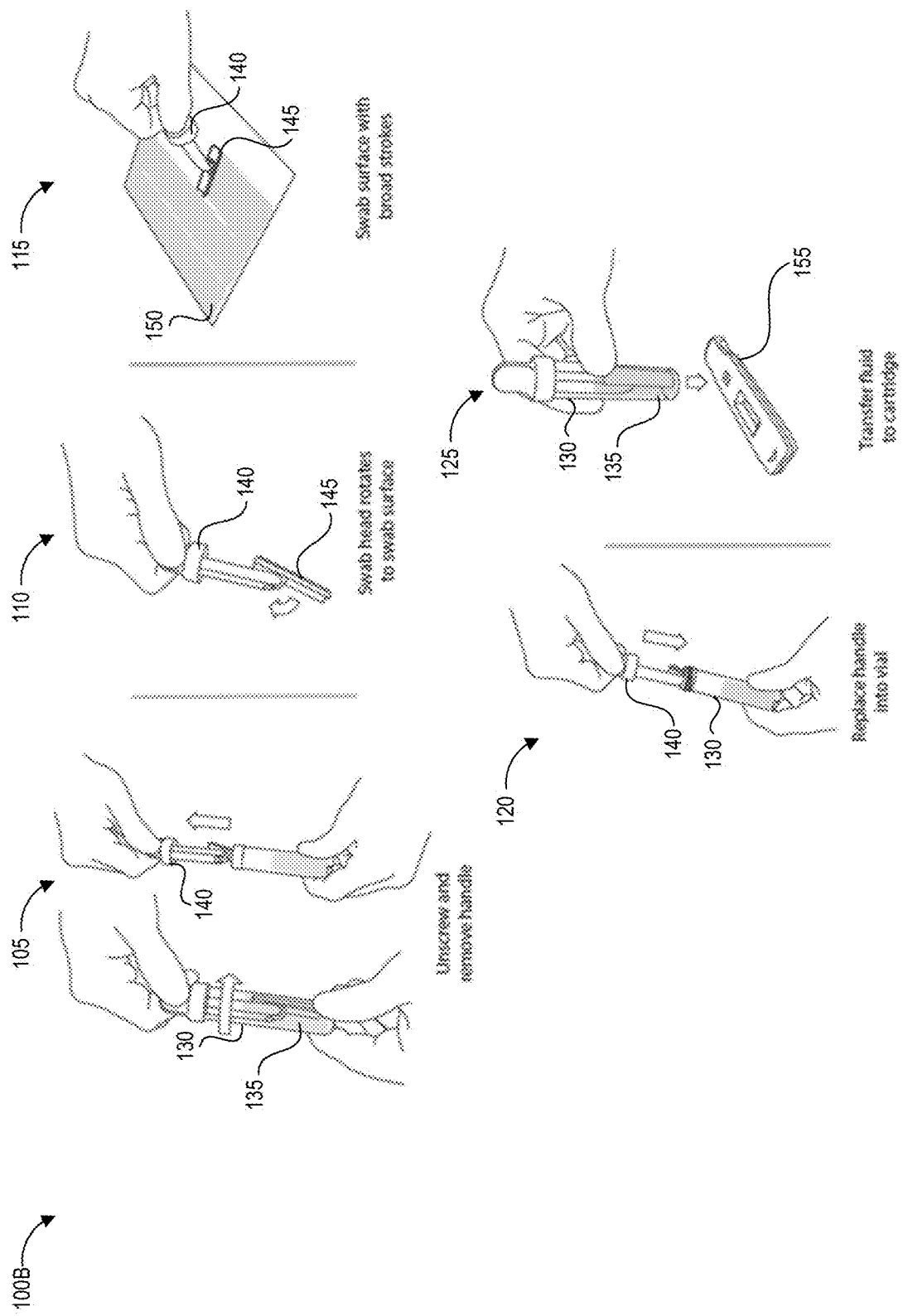

FIG. 1B illustrates another testing method 100B that depicts details of steps 103, 104, and 106 of the process 100A using an alternate embodiment of the collection device.

The method 100B begins at step 105, in which a user can remove a handle 140 from a container 130 containing a predetermined volume of buffer fluid 135. The handle 140 has a swab 245 secured to one end that is pre-wetted with the buffer fluid 135. In other implementations, the user can separately apply a fluid that did not originate from the container 130 to the test surface. For example, the buffer fluid 135 can be provided separately, applied to the test surface, and absorbed using the swab 145. The buffer fluid 135 helps lift contaminants from the test surface into the swab.

At step 110, optionally in some embodiments the swab head can rotate to assist in making and maintaining contact between the swab 145 and the test surface 150.

At step 115, the user can swab a designated test area of the test surface 150. It can be preferable in some implementations to swab the entirety of the test area and only within the test area so as to generate an accurate measurement of the concentration of the contaminant, particularly for contaminants where even small quantities per area are harmful to users. The disclosed templates can be used to assist with demarcating and manually tracking the swabbed area. Swabbing the entirety of the test area and only within the test area can also allow a reader device as described herein to generate an accurate measurement of the concentration of the contaminant per unit area in situations where a very small amount of contaminant is present. Even if the amount of contaminant detected is very small and not immediately harmful to persons in the immediate area, detection of contaminant in any amount can alert the user to a leak or unintended release of hazardous material. Further, for some hazardous drugs there is no safe exposure level. As such, some embodiments of step 115 can involve adhering a template to the test surface to provide an area demarcation over the test area to assist the user with swabbing only a predetermined area, and can further involve using markings on the template border to manually constrain and affirmatively guide the user's actions to increase the likelihood that the entire demarcated area is swabbed in a manner that optimizes the test result, including detection and quantification of a contaminant present in the demarcated area.

At step 120, the user can replace the swab 145 and handle 140 into the collection container 135. Optionally, the user and/or structure of the container can agitate the swab to release collected contaminants into the fluid within the container 135.

At step 125, the user can transfer fluid to a test device, such as but not limited to a cartridge 155 containing a lateral flow assay including a test strip. For example, the user can drip fluid from the container 130 onto a sample receiving zone of the test strip. In some embodiments, the cartridge 155 (or other test system) and container 130 can be structured to mechanically mate via a fluid-tight connection so as to prevent accidental exposure of potentially contaminated fluid to users and/or the testing environment.

Figure 1C:
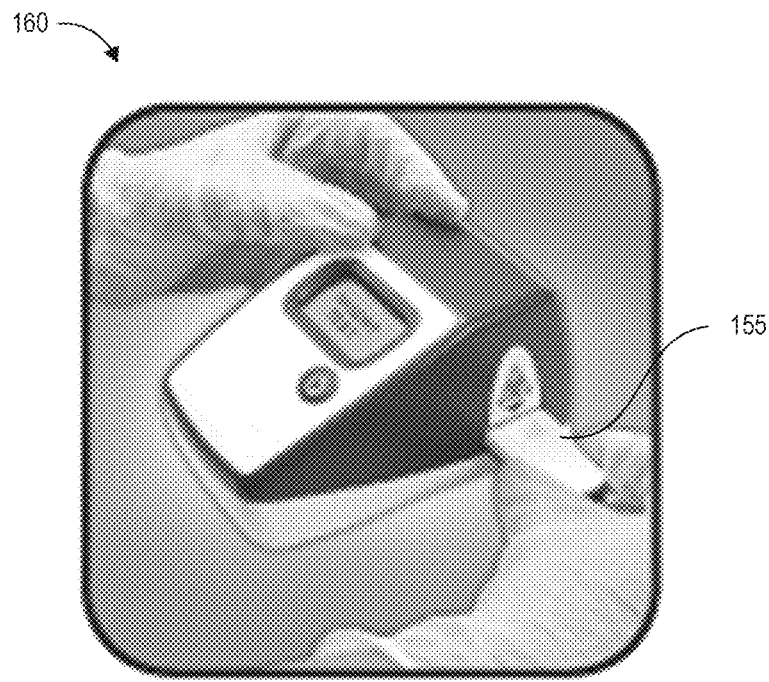
Figure 1D:
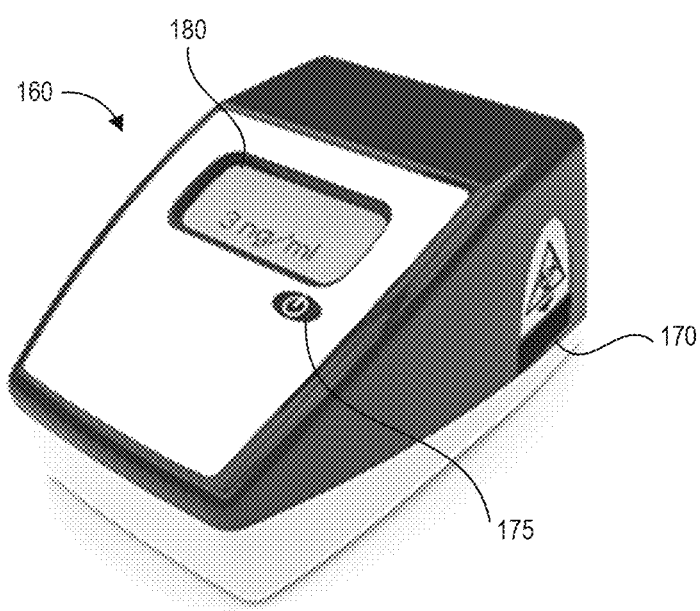

FIG. 1C illustrates a further step of inserting the cartridge 155 into an aperture 170 of reader device 160. Although the following example is described with reference to reader device 300, an assay test device (whether housed within cartridge 320 or not housed within a cartridge) can be read by any suitable reader as described above. Further, though not illustrated, further steps can include operating the reader device 160 to detect a result of the test (for example, by imaging the test strip or detecting an optical change that occurred on the test strip), analyze the test result, and display results of the test. FIG. 1D illustrates the reader device 160 displaying a test result on display 180. In this case, the test result indicates a concentration of the analyte of interest of 3 ng/ml.

The device 160 can be an assay reader device having an aperture 170 for receiving an assay test strip and cartridge 155 and positioning the test strip so that the detection zones are positioned in the optical path of detection components located inside the device 160. In some cases, the detection components can include imaging components that image portions of the assay test strip and cartridge 320 to detect optical changes in the assay test strip. The device can also use these or additional imaging components to scan a bar code on the cartridge, for example to identify which detection techniques and analysis to perform.

Some embodiments of the device 160 can be configured to perform an initial scan using a barcode scanner to scan one or more bar codes, for example provided on templates (or barcode keys separate from the templates but provided with the templates), on cartridges inserted into the aperture 170, or on separate identifiers. A barcode can identify the type of test to be performed, the template used for sampling, the person conducting the test, the location of the test, and/or the location in the facility of the test surface (for example pharmacy, nursing area, cabinet #, bed #, chair #, pump #, etc.). After reading any barcode identifiers the cartridge 155 is then inserted into the reader as shown in FIG. 1C. Barcodes are provided as an illustrative example, and in various embodiments other identification patterns can be provided for reading by the device 160, for example serial numbers, graphical identifiers, radio frequency ID transmitters, and the like.

The device 160 can include a button 175 that readies the device for use and provides an input mechanism for a user to operate the device. In some embodiments device operation mode can be set via a number or pattern of clicks of the single button 175 of the device 160. For example, in some implementations a single press of the button 175 can power on the device 160 and set the device 160 to a default operation mode, and the device 160 can implement the default operation mode upon insertion of a cartridge. A double click of the button 175 can initiate an alternate operation mode that is different than the default operation mode. Other numbers or patterns of pressing the single button 175 by a user can provide instructions to the processor of the device regarding a desired operation mode. Embodiments of a device 160 are described herein with reference to a single button, but other features allowing a user to select and switch between device operation modes are possible (such as but not limited to a single switch, knob, lever, or handle).

One example of a device operation mode is end-point read mode. In the end-point read mode, the user prepares and incubates the assay outside of the device 160 and tracks the development time of the assay. For example, an assay for determining Methotrexate or Doxorubicin concentration can have a development time of 5 minutes, so the user would apply the fluid to the assay from a collection device as described herein and wait for 5 minutes. At the end of the 5 minutes the user would insert the assay 155 into the device 160 to obtain a test result. Accordingly, when operating in end-point read mode the device 160 can provide instructions, for example audibly or on a visual display, that instruct a user to wait for a predetermined time after applying a sample to an assay before inserting the assay in the device 160. In other embodiments, when operating in end-point read mode, the device 160 may not display any instructions but may simply read an assay upon insertion into the device 160. Upon insertion of the assay into the base device 160, an optical reader of the device can collect data (for example, image data) representing the assay for analysis in determining a result of the assay. In some embodiments end-point read mode can be the default operation mode of the device 160.

Another example of a device operation mode is walkaway mode. When operating in walkaway mode, the device 160 can provide instructions for the user to insert the assay immediately after application of the sample. In the walkaway mode according to one embodiment, the user can apply the specimen to the assay and immediately insert the assay into the device 160. The assay will develop inside the device 160 and the device 160 can keep track of the time elapsed since insertion of the assay 155. At the end of the predetermined development time, the device 160 can collect data representing optical changes in the assay, analyze the data to determine a test result, and report the test result to the user. The assay development time can be unique to each test. In some embodiments walkaway mode can be set by double-clicking the single button 175 of the device 160. Further input can indicate the assay development time to the reader device. For example, a barcode scanned by a barcode reader, or a barcode provided on the assay or on a cartridge used to hold the assay, can indicate to the device 160 a type of assay that is inserted and a development time for that assay. Based upon the type of assay, the device 160 can wait for the predetermined amount of time after sample application and insertion before collecting data representing optical changes in the assay.

There are many advantages associated with the ability of a user to select and switch between device operation modes in implementations of assay analyzers described herein. The endpoint read mode can be convenient in large laboratories or medical practice facilities where personnel typically batch process a number of tests. The walkaway mode can be useful when a single test is being performed, or when the end user does not want to have to track the assay development time (or is not knowledgeable or not trained on how to track the assay development time accurately). The walkaway mode can advantageously reduce or eliminate the occurrence of incorrect test results due to an assay being inserted and read (for example, imaged) too quickly (too soon before the development time of the assay has elapsed) or too slowly (too long after the development time of the assay has elapsed). Further, in walkaway mode the assay reader can operate to inspect the assay (for example, capture multiple images of the assay) at predetermined time intervals, for example when a kinetic graph of the assay readings is desired.

One embodiment of the disclosed device 160 includes only a single button 175 on its exterior housing, such as a single power button that powers the device 160 off and on. Embodiments of the disclosed device 160 also implement two different device operation modes (although more than two device operation modes are possible). In order to enable the end user to select and switch between the two device operation modes, the device 160 can include instructions to implement a double-click function on the power button. After receiving input of a single press of the button to power on the device, insertion of an assay cartridge can automatically trigger end-point read mode. When the processor of the device receives input from a user double clicking the power button, this can initiate the stored instructions to implement the walkaway mode. This double click functionality offers a simple and intuitive way for the end user to switch between different operation modes of the base assay analyzer. The double click functionality also enables the user to configure the device in real time to operate in the walkaway mode without requiring any additional configuration steps or additional programming of the device 160 by the user. It will be appreciated that the device 160 can be provided with instructions to recognize other click modes instead of or in addition to the double click to trigger secondary (non-default) device operation modes, for example to recognize a user pressing the button any predetermined number of times, pressing the button in a predetermined pattern, and/or pressing and holding the button for a predetermined length of time.

As described above, the device 160 can also include a display 180 for displaying instructions and/or test results to the user. After insertion of the test strip, the device 160 can read a bar code on the assay test strip to identify the name, permissible concentration ranges of the drug, and/or maximum permissible concentration of the drug. The device 160 can inspect the inserted test strip (in one example, by "imaging" the strip or otherwise emitting light towards the test strip and then detecting the intensity of a signal representing detected light reflected from the test strip), and analyze the signals representing the inspected test strip to calculate results, display the results to the user, and optionally transmit and/or locally store the results. The results can be calculated and displayed as contamination with an indication of positive or negative (for example, +/−; yes/no; etc.), and/or the actual amount of contamination (analyte of interest) per area (for example, Drug Concentration=0.1 ng/cm$^2$) and/or an actual an actual contamination (analyte of interest) per area (for example, Drug Concentration=0.1 ng/cm$^2$), and/or an actual amount of contamination (analyte of interest) per volume of buffer solution (for example, Drug Concentration=3 ng/ml). These indications are non-limiting examples as other indications and measurement units are also suitable.

Some embodiments of the device 160 may simply display the result(s) to the user. Some embodiments of the device 160 may also store the result(s) in an internal memory that can be recalled, for example, by USB connection, network connection (wired or wireless), cell phone connection, near field communication, Bluetooth connection, and the like. The result(s) can also automatically be logged into the facility records and tracking system of the environment (for example, facility) where the test is performed. The device 160 can also be programmed to automatically alert any additional personnel as required, without further input or instruction by the user. For example, if the device 160 reads contamination levels that are above the threshold of human uptake and considered hazardous to for human contact, a head pharmacist, nurse, manager, or safety officer can be automatically notified with the results and concentration of contamination to facilitate a rapid response. The notification can include location information, such as but not limited to a geographic position (latitude/longitude) or description of location (Hospital A, Patient Room B, etc.). That response may include a detailed decontamination routine by trained personnel or using a decontamination kit provided together or separately from the hazardous contamination detection kit.

In some embodiments, device 160 can be a special-purpose assay reader device configured with computer-executable instructions for identifying trace concentrations of contaminants in the samples applied to test strips. In other embodiments other suitable liquid sample test systems can be used to identify the presence and/or concentration of a hazardous drug.

Overview of Example Devices and Techniques for Test Area Sampling

As described above, thoroughly and accurately collecting a sample from a known area can be beneficial or required in order to accurately determine the presence or concentration of trace quantities of hazardous drugs in a test sample. Existing sampling systems require the test operator to measure out test area dimensions and place four adhesive dots on the test surface at the corners of a rectangular test area. This approach has a number of drawbacks including requiring a lengthy setup, being subject to measurement and marker placement errors, not providing a border that completely surrounds the test area, lacking any guidance for how to sample the test area, and increasing the risk of exposure of the test operator to potential hazardous drug contamination through placement and removal of numerous adhesive markers.

The disclosed templates address this problem by providing an adhesive border defining an open area that, when the template is adhered to the test surface, demarcates an area of a test surface for sampling. The border can be quickly and easily adhered to the test surface, providing a single adhesive marker that demarcates the entire border of a precisely-defined test area of known dimensions, and then peeled away once sampling is completed. Such templates can be provided with alignment marks around the interior edge of the border to guide the user to perform optimal swabbing motions (which optimize, for example, the likelihood that all trace contaminants, if present, will be collected on the swab and that the total area that is actually swabbed is the same as or substantially the same as the test area of known dimensions demarcated by the border). The disclosed templates include a first inner portion and a second outer portion, wherein the first inner portion is separated from the second outer portion prior to adhering the second outer portion to the test surface. Separating the first inner portion from the second outer portion forms the border defining the precisely-defined test area of known dimensions. Some embodiments can additionally provide step-by-step graphical instructions for sampling procedures in the first inner portion that a user separates from the second outer portion prior to adhering the second outer portion to the test surface. Advantageously, the disclosed templates provide both area demarcation and visual guidance for alignment of swabbing motions without requiring a user to perform extra testing steps, thereby minimizing contact between the user and the sample.

Figure 2A:
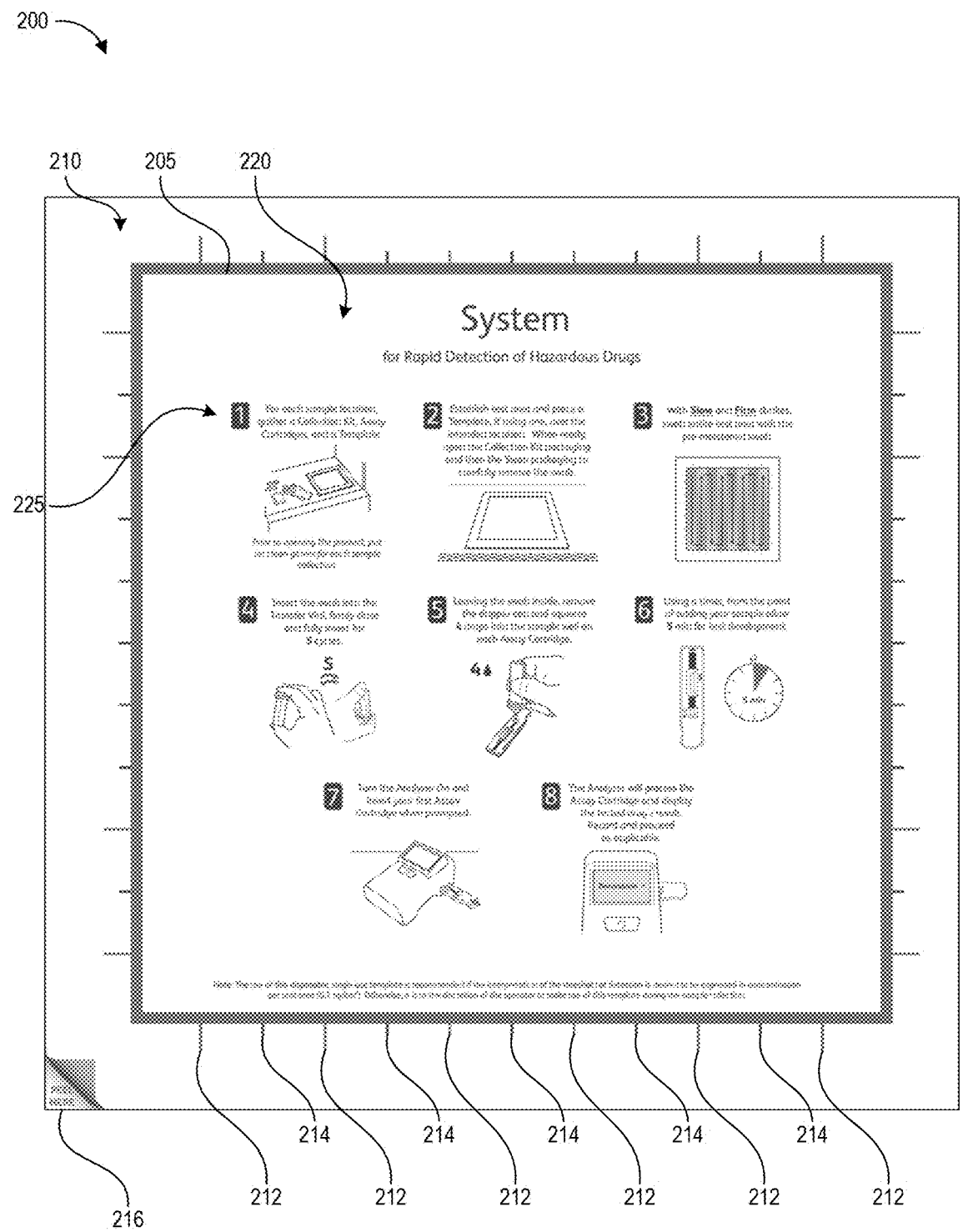
FIGS. 2A-2C illustrate an example template as described herein.
Figure 2B:
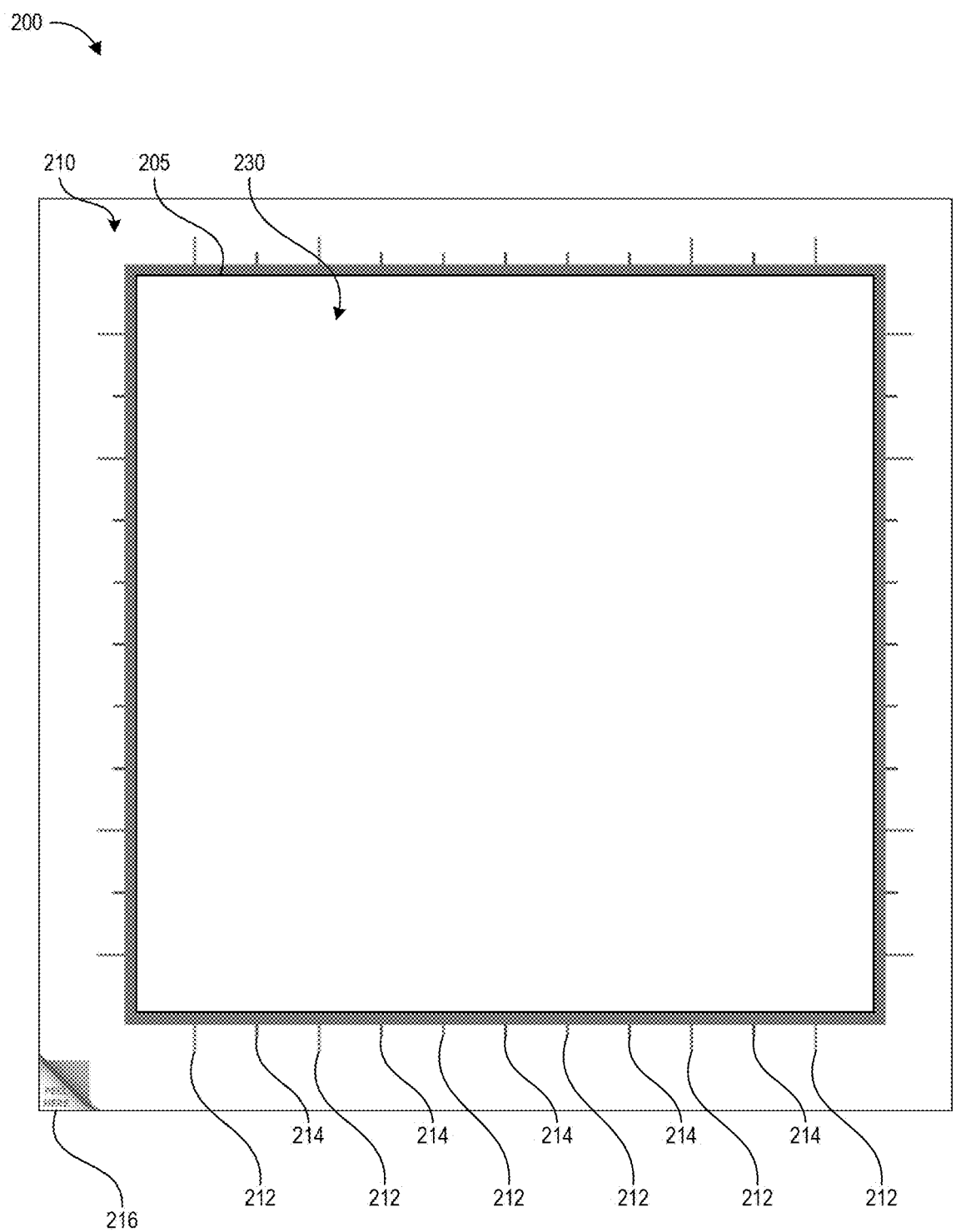
Figure 2C:
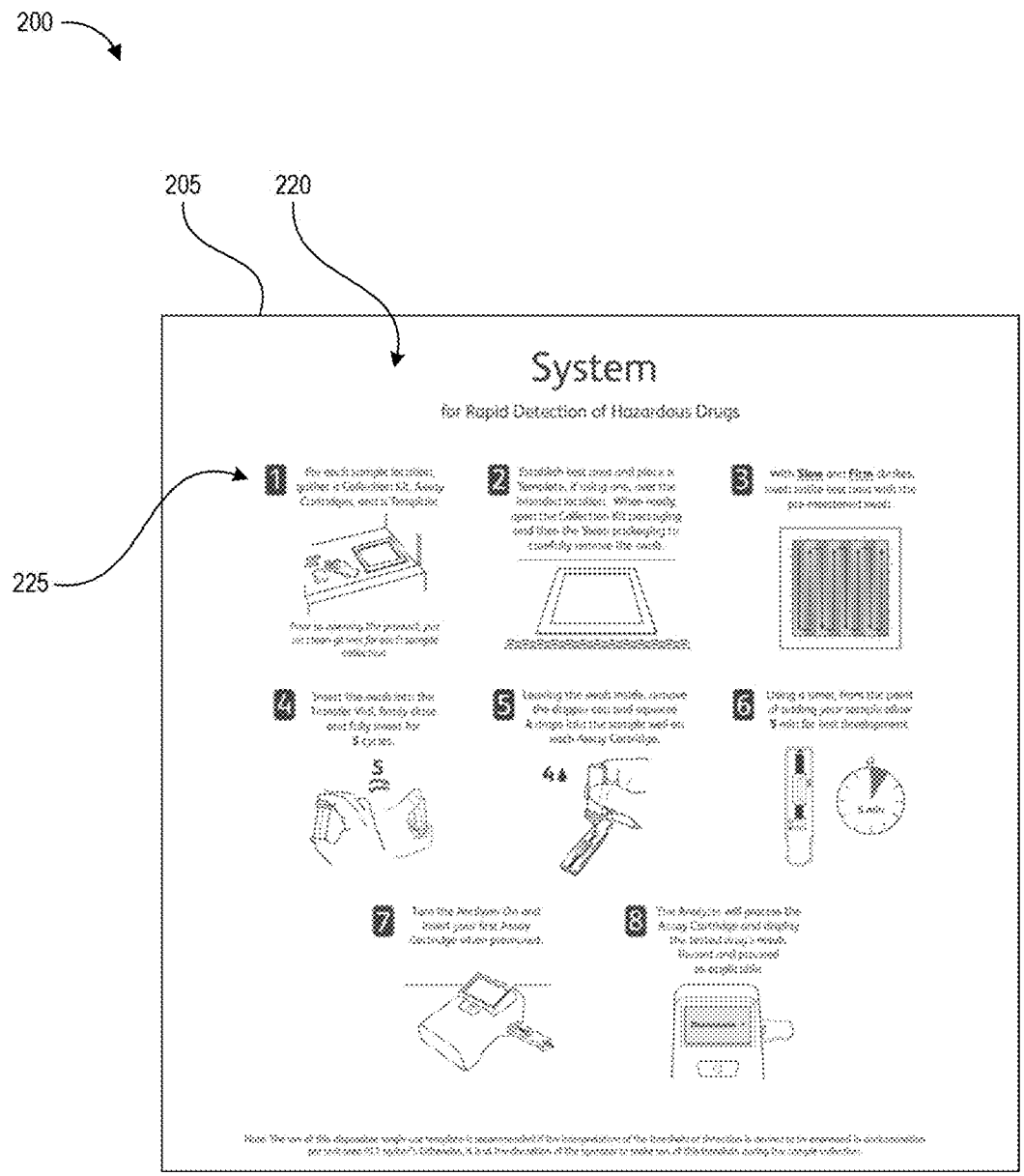

FIGS. 2A-2C illustrate an example template 200 as described herein. FIG. 2A illustrates the template prior to use. The template includes second outer portion 210 (hereinafter "border 210") and a removable first inner portion 220 (hereinafter "removable portion 220") that is separable from the border 210 along separation line 205. In one non-limiting example, the template 200 is packaged in a sterile and heat-sealed polymer pouch, and provided to a user in a kit with other tools for the hazardous drug sampling and/or testing processes (e.g., a swab, a collection container, one or more assays, and a test device). The template can be packaged as shown in FIG. 2A as a solid square, with the removable portion 220 cut (fully or via spaced perforations) from border 210 along the separation line 205 but in contact with the border 210 due to both pieces being removably secured to a protective backing layer. In one non-limiting example, the outer perimeter of the border 210 (and the template 200) measures about 15 inches by about 15 inches and the perimeter of the removable portion 220 measures about 12 inches by about 12 inches.

The border 210 and removable portion 220 can be formed from a thin substrate, for example paper or a film or sheet of polymer. The substrate can be flexible in some embodiments such that a user may bend the substrate, for example during application of the border to a test surface, without causing wrinkles or fractures in the border. In other embodiments, the substrate can be a sheet of material with suitable rigidity for maintaining the shape of the open area demarcating the test area. In some embodiments, the substrate used for the border 210 may have higher rigidity than the substrate used for the removable portion 220 such that the border remains flat while the removable portion 220 is flexible. In some embodiments, the substrate can be pre-folded along fold lines that enable the template to occupy a smaller area, for example for shipping in a kit. The substrate can be planar in some embodiments. In other embodiments, the substrate can be formed in a non-planar (e.g., angled or contoured) shape that matches the profile of a test surface so that the edges of the open area follow the shape of the test surface and lie flush against the test surface. The substrate can maintain its shape during swabbing of the test area, even if the swab contacts the substrate. In the illustrated embodiment, the outer portion of the border 210 is in the shape of a square frame and the removable portion 220 is in the shape of a closed square. The border 210 and the removable portion 220 can be formed in any suitable geometric shape, however. Further, the shape of the removable portion 220 need not mirror the shape of the border 210, for example in order to demarcate a test area of a particular desired shape. In one non-limiting example, the outer perimeter of the border 210 is in the shape of a circle and the removable portion 220 is in the shape of a rectangle.

FIG. 2A illustrates the surface of the template that would face a user with the template positioned on a test surface. As illustrated, this surface is provided with a number of printed elements including graphical sampling instructions 225, wiping alignment markers 212, 214, and corner peel indicator 216. Though not illustrated, a barcode serial number, or other identification marker can be printed on the surface of the border 210 or removable portion 220 in order to identify the template and the surface area of the open area 230 to a test device. In some embodiments, for example embodiments of the template 200 that use a paper or other absorbent substrate, the portion of the surface facing the user can be covered with a protective coating such as polypropylene laminate in order to prevent buffer solution applied to the test surface during sampling from being absorbed into the upper surface of the template. Beneficially, in implementations designed to permanently or semi-permanently adhere the template to the test surface, this can allow a user to clean the template 200 by wiping it down and protects the printed ink. Even in implementations that remove the template from the test surface after sample collection, the protective coating can prevent buffer solution from causing the ink to bleed.

The opposing surface (e.g., the surface that directly contacts the test surface) can be provided with an adhesive (including but not limited to an adhesive layer) to adhere the template to a test surface. In various embodiments, the adhesive may be configured for easy removal of the template 200 from the test surface after sampling. For example, the adhesive may be a weak adhesive that allows a user to peel off the template from the test surface after sampling with just two fingers gripping one corner. Alternatively, the adhesive may be a stronger adhesive to permanently or semi-permanently adhere the template to the test surface. As an example, some embodiments may be provided with a pressure-sensitive adhesive such as a silicone adhesive or a polymer emulsion adhesive (e.g., acrylic emulsion). The adhesive can be protected by a removable protective layer prior to use, for example a waxy paper or plastic film.

The substrate can be scored or cut along the separation line 205, for example as a continuous line or spaced-apart perforations, and such scoring can extend through just the substrate or in some embodiments also through the protective backing layer. The corner peel indicator 216 can be positioned over an area of the border 210 that is not provided with adhesive to indicate to the user where the substrate of the border 210 can easily be separated from the protective layer. Other embodiments may be manufactured from a material that utilizes static electrical forces to cling to the test surface, for example a thin plastic film, and in such embodiments the adhesive and protective layer can be omitted.

FIG. 2B shows the border 210 with the removable portion 220 removed to create an interior open area 230 for demarcating the test area. In some embodiments the four sides of the border 210 can have uniform thickness, for example spanning a thickness of at least 1.5 inches from the inner perimeter of the border 210 formed by the separation line 205 to the outer perimeter. In some embodiments the sides of the outer perimeter can be about 15 inches long, and the sides of the inner perimeter can be about 12 inches long to demarcate a one foot square open area 230. As illustrated, in some embodiments two of the sides of the border 210 can be thicker (in this case, the left and bottom sides) than the other two sides (in this case, the right and top sides), however the minimum thickness may still be at least about 1.5 inches and the open area 230 can still be a 12 inch by 12 inch square. The border thickness of at least 1.5 inches can provide sufficient material for the user to control the border 210 during application to the test surface. Other sizes of the template border 210 can be used in other embodiments.

The inner perimeter of the border 210 formed by the separation line 205 has four edges defining the open area 230. The open area 230 includes negative space bounded by the inner perimeter of the border 210 and defines a test area to be swabbed by the user. The size of the open area can vary in different implementations of the template based on the requirements of the sampling procedure. Buffer solution can be applied to the test area within the open area of the template, for example a buffer solution formulated to pick up the hazardous drug of interest. The buffer solution can be applied by wiping a pre-moistened swab to the test surface in such a way that buffer solution is expressed onto the test surface, and/or the buffer solution can be poured onto the test surface from a container. In one non-limiting example, the buffer solution can flow along the test surface within the open area of the template with its flow path bounded by the interior edges. Beneficially, this can contain the buffer solution within the test area and potentially prevent hazardous contamination from spreading.

Some or all of the surface of the border 210 that is configured to be applied against the test surface can be coated with adhesive for securing the border 210 to the test surface. Advantageously, this adhesive can prevent buffer solution from moving outside the perimeter of the open area 230. Beneficially, adhering the border 210 to the test surface can prevent the border 210 from moving during sampling, for example in response to contact between the swab/handle and the border. If a user bumps an unsecured border 210 and moves it across the test surface during sampling, then the actual area sampled is unknown even though the area of the open area 230 is known, because the open area 230 has moved to a new location on the test surface during sample collection. This can cause the user to sample from a larger area of the test surface than the open area 230 as the template border 210 slides over new areas. Maintaining a fixed location for the open area 230 can be advantageous for determination of accurate test results, as it constrains the actual area swabbed to the known area of the open area 230. Fixing the border 210 to the test surface via an adhesive (or static cling) can beneficially keep the hands of the user away from the potentially contaminated surface and any buffer liquid used during the sampling, as the user does not have to manually apply pressure to the border 210 to keep it in place. The adhesive can have sufficiently high tack to keep the border 210 in place when contacted by the swab as it is moved by the user during sampling. Some embodiments can also have sufficiently low tack to allow the user to easily peel the border 210 off of the test surface when sampling is complete.

In this embodiment, the alignment markers 212, 214 extend from the separation line 205 outward towards the outer edges of the template. Other configurations are suitable. Such alignment markers can visually assist a user to thoroughly and accurately sample the entire area demarcated by the open area 230. For example, a first set of the alignment markers 212 depicted with a first representation can indicate to the user to keep a center of the swab aligned with the marker and a second set of the alignment markers 214 depicted with a second, different representation can indicate to the user to keep the edges of the swab aligned with the markers. In the illustrated embodiment, the first representation is a first line having a first length and the second representation is a second line having a second length less than the first length. In addition, in the illustrated embodiment, the first representation includes a first color (in this non-limiting example, orange) and the second representation includes a second, different color (in this non-limiting example, blue). The user can wipe the test surface in a relatively straight line while maintaining the alignment of the swab and the markers, and then can move the swab into alignment with the next adjacent set of markers, as discussed in more detail with respect to FIG. 3B below. In this manner, the template guides the user to perform swabbing in a controlled, constrained, and precise manner that samples the entirety of the test surface. Though depicted as lines, the alignment markers 212, 214 can include dots, bands of color or patterns, or other graphical representations suitable for visually indicating a wiping path to the user. Some embodiments can include a single set of alignment markers rather than different first and second sets 212, 214.

FIG. 2C shows the removable portion 220 after it has been removed from the border 210 along the separation line 205. As illustrated, the removable portion 220 is provided with a graphical series of sampling steps 225 similar to those discussed above with respect to FIG. 1A. Without such instructions, the area occupied by the removable portion 220 would be blank and potentially of little or no use to the user. The presently-disclosed template design advantageously uses this material to provide the user with sampling procedure instructions that are immediately visible at the start of the sampling procedure and easily accessible by the user throughout the time of sampling with the template 200.

Beneficially, some embodiments of the removable portion 220 can include an adhesive layer provided across some or all of the surface that makes contact with the test surface (opposing the illustrated surface), similar to the border 210. This can enable a user to secure the graphical instructions near the test surface, for example on a wall, cabinet, pharmacy hood, or other structure adjacent to or near the test surface. The instructions can be durable, for example coated with a protective coating, and in some embodiments the adhesive can have sufficient tack to permanently or semi-permanently adhere the removable portion 220 to the structure near the test surface. In other embodiments the adhesive can have sufficiently low tack to allow the user to easily peel the removable portion 220 away once sampling is complete.

Figure 3A:
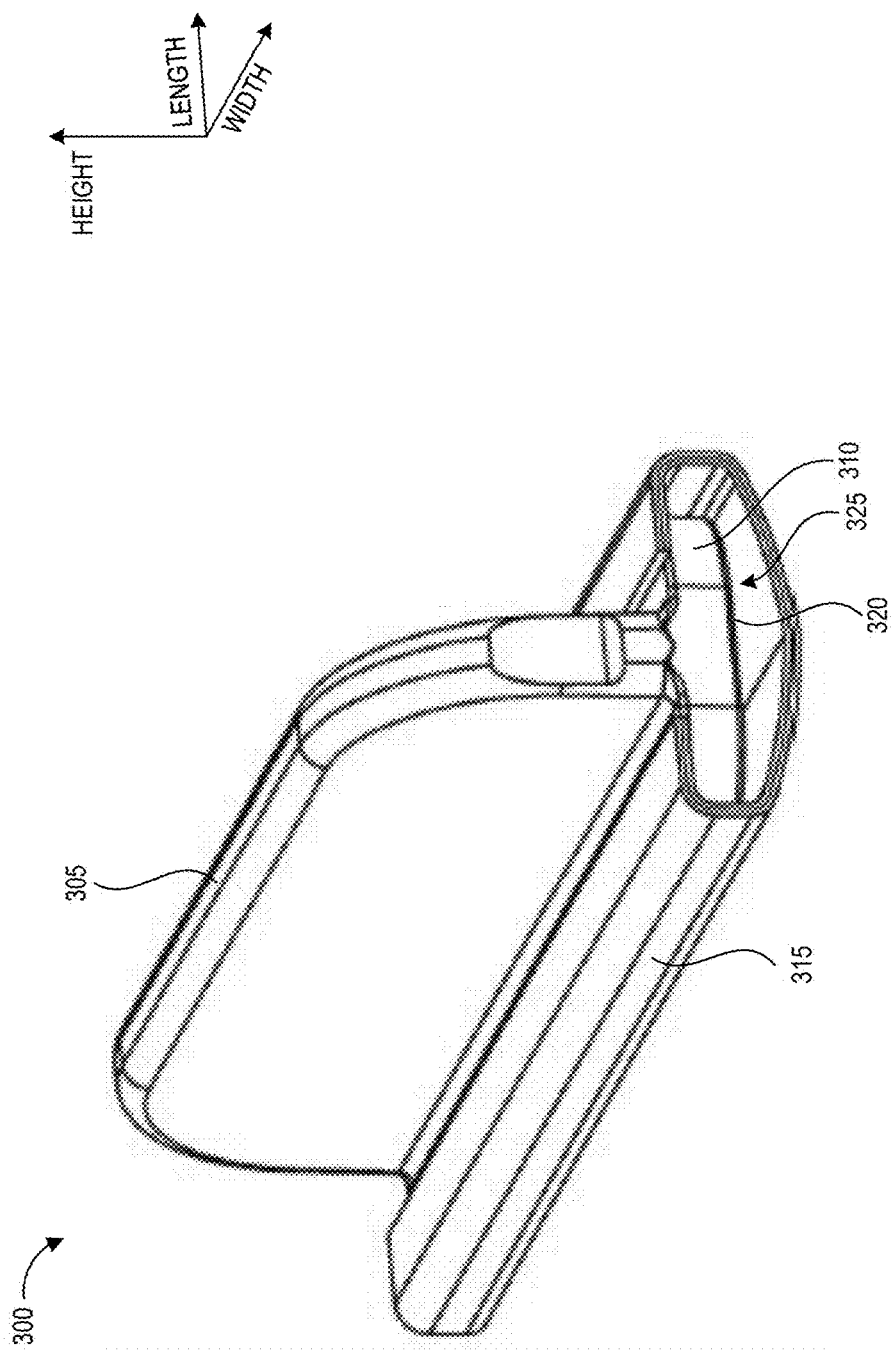
FIG. 3A illustrates an example handle that can be used to sample a test area demarcated by embodiments of the disclosed templates.

FIG. 3A illustrates an example handle 300 secured to swab material 315 that can be used to sample a test area demarcated by embodiments of the disclosed templates. The handle 300 includes a grip portion 305 and a base portion 310 with the swab material 315 wrapped around and secured to the base portion 310, for example via ultrasonic welding, mechanical fasteners, adhesive, or other suitable securing techniques.

As illustrated, the grip portion 305 extends perpendicularly from the center of one face of the base portion 310. The grip portion 305 can extend away from the base portion at other angles and/or from other locations along the width of the base portion 310 in other embodiments. The grip portion 305 can have a height sufficient to keep the fingers of a user away from a surface in contact with the swab material secured to the base portion 310, for example 0.25 inches or more, or 0.5 inches or more, in various embodiments. In one non-limiting example, the height of the grip portion 305 is about 0.525 inches. The grip portion 305 can extend along the full width of the base portion 310 as illustrated, or can extend along just a portion of the width of the base portion 310. In some embodiments the length of the base portion can also assist in shielding the fingers of the user from the test surface, and the length can be for example 0.25 inches or more, or 0.5 inches or more, in various embodiments. In one non-limiting example, the length of the base portion 310 is about 0.55 inches. Embodiments of the base portion 310 with a length of about 0.55 inches can include about 0.2 inches clearance on each side of the grip portion 305 for the user's fingers to grip the handle 300. This can shield the user's fingers from the test surface below the base portion 310 during use of the handle 300, and can, for example, act as a stop to prevent the user's fingers from contacting the test surface. Other sizes can be suitable for other embodiments, and the disclosed dimensions are provided to illustrate and not limit the dimensions of the handle 300.

The swab material 315 is configured to be loose enough to form a gap 325 between the swab material 315 and the adjacent surface of the base portion 310. The gap 325 can enable the swab material 315 to be agitated by buffer solution when shaken within a collection vial in order to extract collected contaminants from the swab material 315. The gap 325 can be between 0.25 inches and 0.75 inches in some embodiments. The swab material 315 may be longer than the base 310 of the handle 300 such that around 0.25 inches of swab material 315 extends beyond the edges of the base 310. The base 310 can have a width of around 2 inches in some embodiments.

Figure 3B:
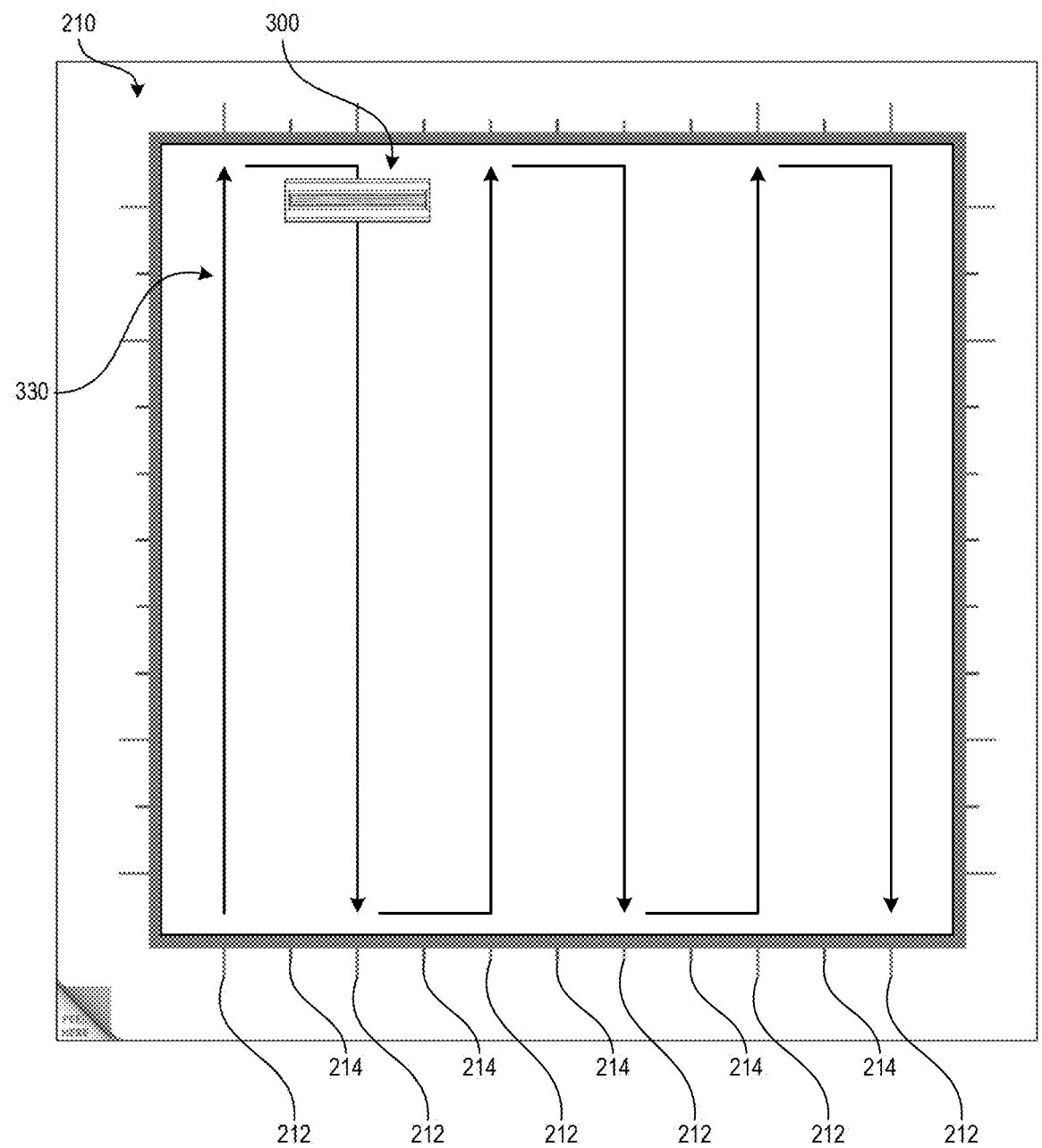
FIG. 3B illustrates an example swabbing pattern using the handle of FIG. 3A with the template of FIG. 2B.

FIG. 3B illustrates an example swabbing pattern 330 using the handle 300 of FIG. 3A within the border 210 of the template of FIG. 2B. As shown, the user can align the center of the width of the handle 300 with one of the first set of alignment markers 212. Two adjacent markers 214 of the second set of alignment markers align with the opposing edges of the width of the base of the handle 300. In this non-limiting embodiment, the swab material extends a small distance beyond these edges of the base of the handle 300. In one example, adjacent markers are positioned 1 inch apart, with the first and last markers 212 are each positioned 1 inch from the adjacent interior edge of the border 210. This corresponds to an open area of 12 inches by 12 inches, and in such embodiments the base of the handle 300 can have a width of 2 inches. In such embodiments, with six precise, linear strokes (as shown by the swabbing pattern 330), the user can sample the entire test surface exposed through the border 210 with precision and minimal deviation from the optimal swab pattern.

The user can begin swabbing with the center of the handle 300 aligned with a first alignment marker 212. The user can move the handle 300 in a straight line between the first alignment maker 212 on a first interior edge of the border 210 and a corresponding alignment marker on the opposing interior edge of the border 210. The handle 300 can be in contact with a third interior edge of the border 210 (in the illustrated embodiment, the leftmost interior edge) during this first swab stroke. Once the user has swabbed from the first interior edge of the border 210 to the opposing interior edge, the user can move the center of the handle 300 into alignment with a next alignment marker 212 and can continue moving the swab in a linear fashion along a second line between that alignment marker and the corresponding alignment marker on the first edge. The swab material extending beyond the edges of the base causes a slight overlap between the areas swabbed when the handle 300 is moved along the first line and the second line, and similarly causes overlap between adjacent lines as the handle 300 is moved according to the pattern 330. This overlap beneficially assists the user in swabbing the entire area of the test surface bounded by the border 210. For example, the overlap allows the user to deviate slightly from the intended alignment and still swab the entire test surface.

Figure 3C:
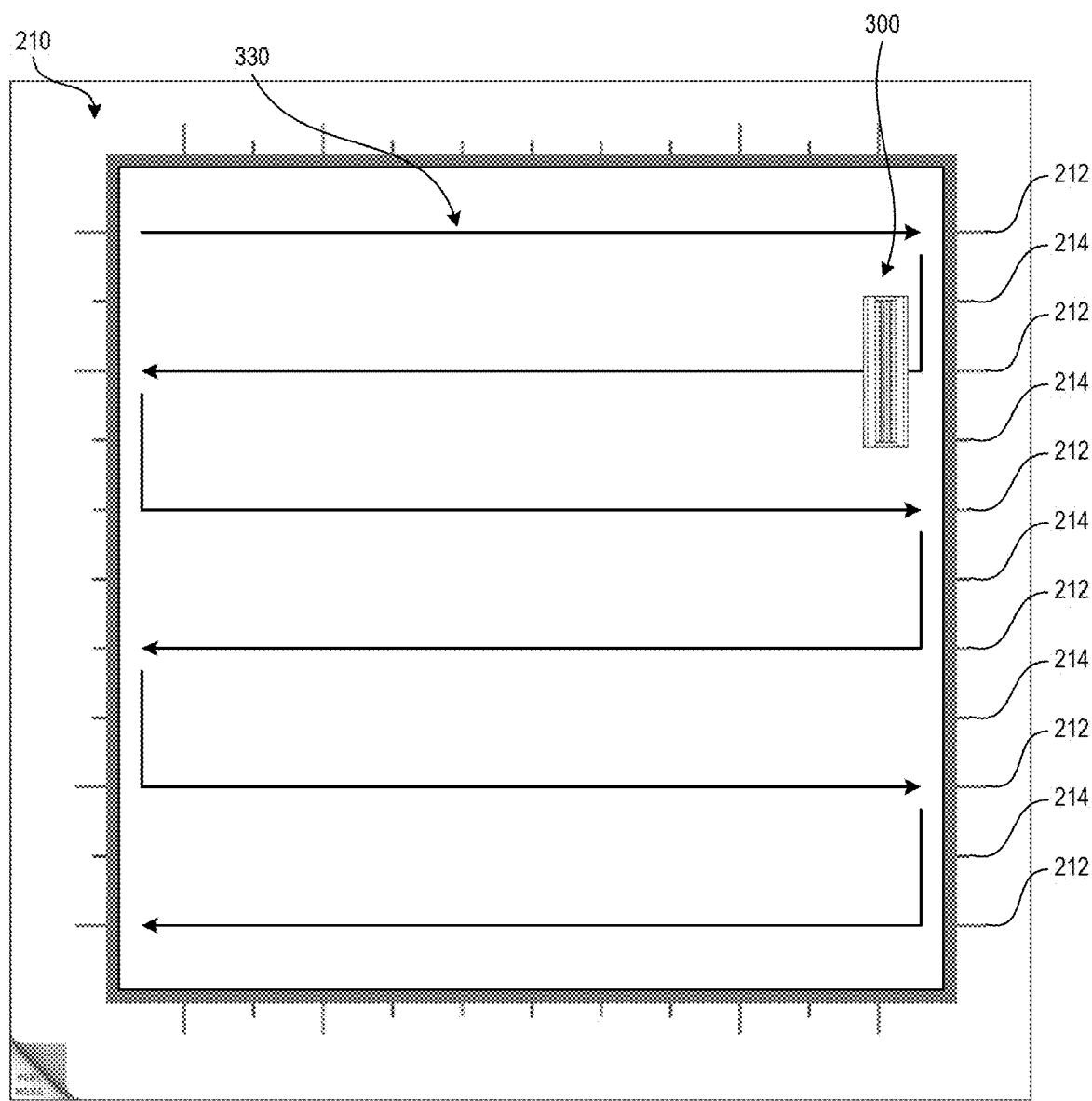
FIG. 3C illustrates another example swabbing pattern using the handle of FIG. 3A with the template of FIG. 2B.

The swabbing pattern 330 described with reference to FIG. 3B is just one example of a suitable swabbing pattern using implementations of templates described herein. Another example swabbing pattern 330 is shown in FIG. 3C, which illustrates swab strokes in a horizontal orientation rather than a vertical orientation.

Figure 4:
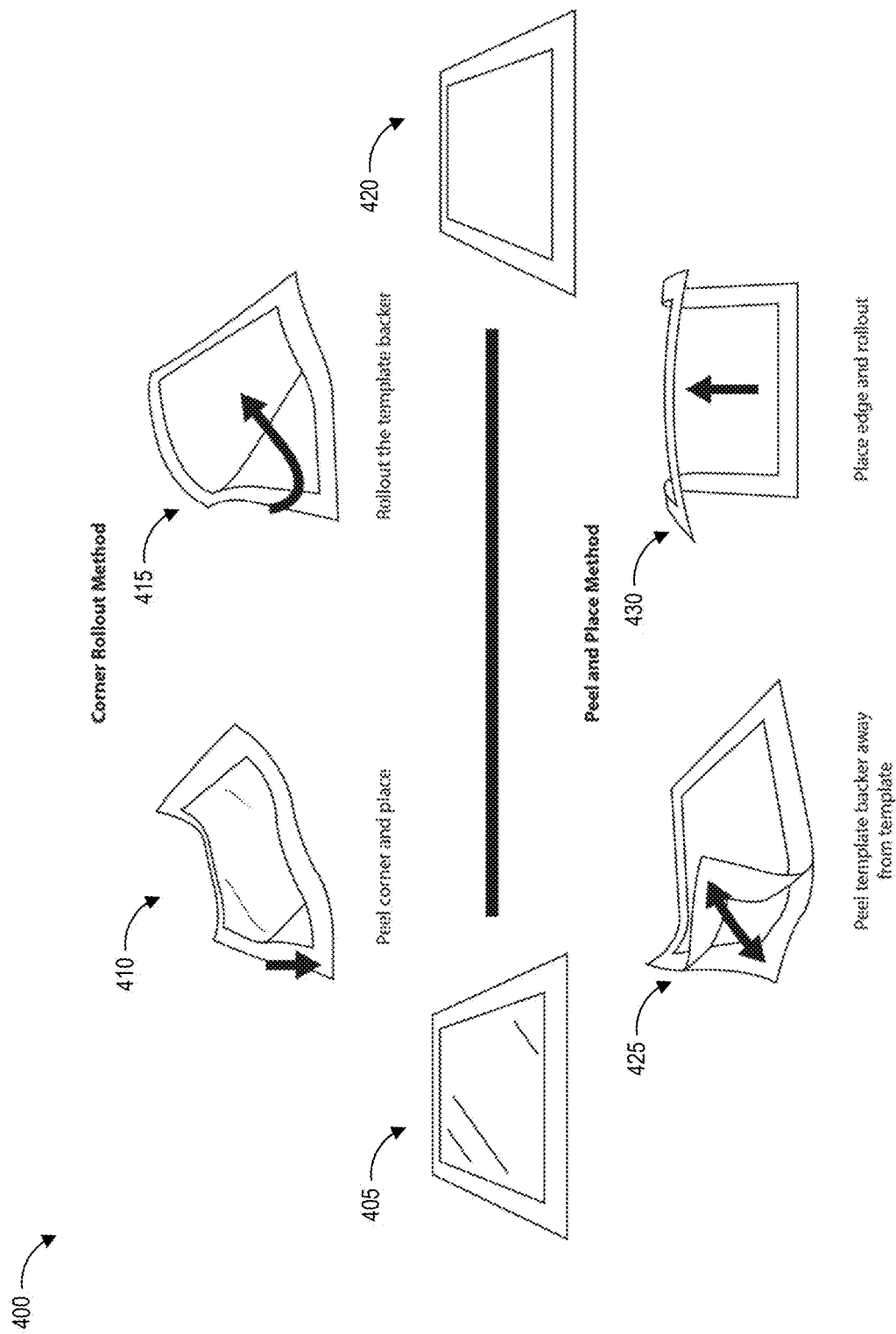
FIG. 4 illustrates example techniques for application of the template of FIGS. 2A-2C to a test surface.
Figure 5A:
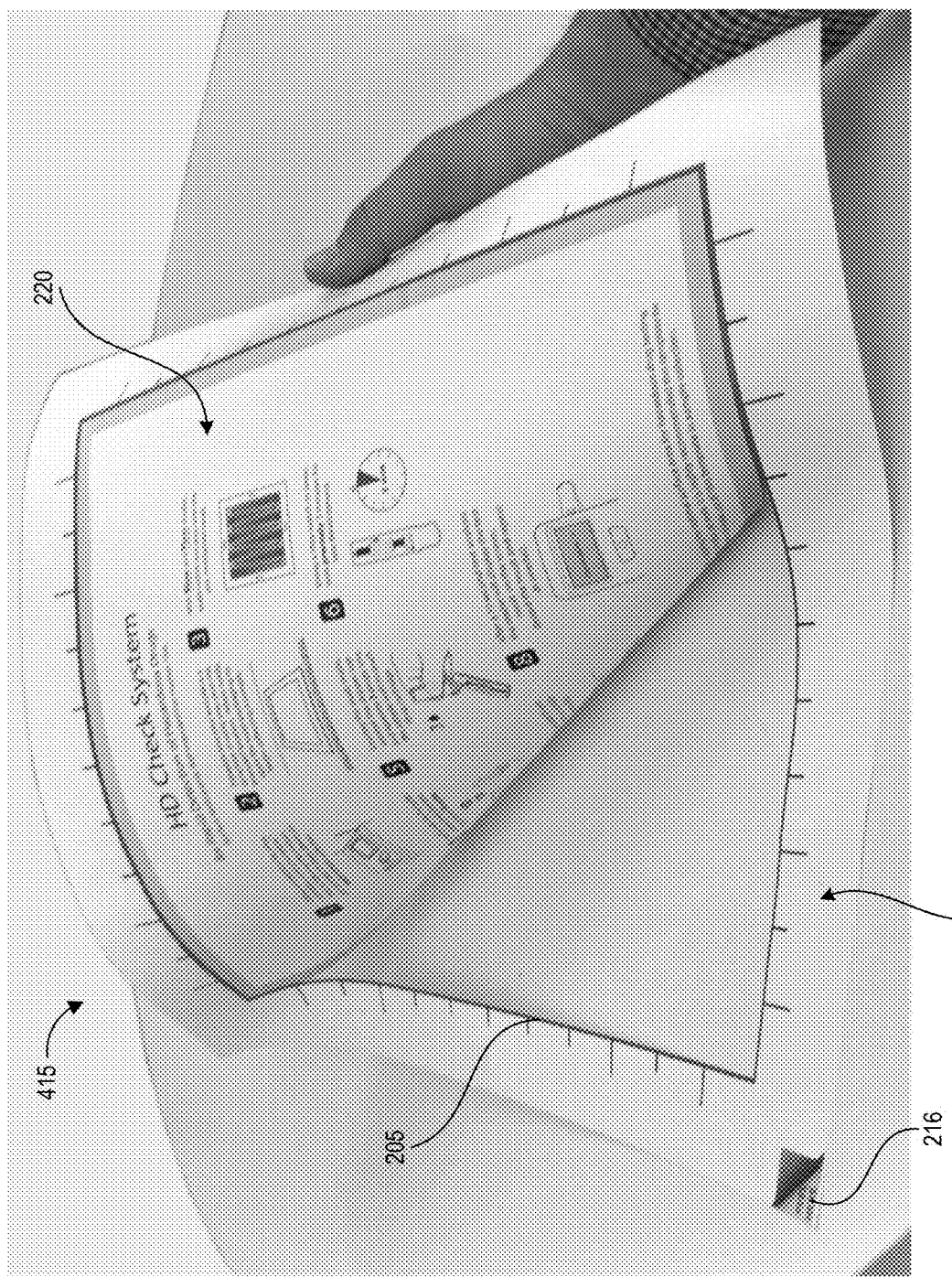
FIGS. 5A and 5B depict photographs of the template of FIGS. 2A-2C at different stages of the application process of FIG. 4.
Figure 5B:
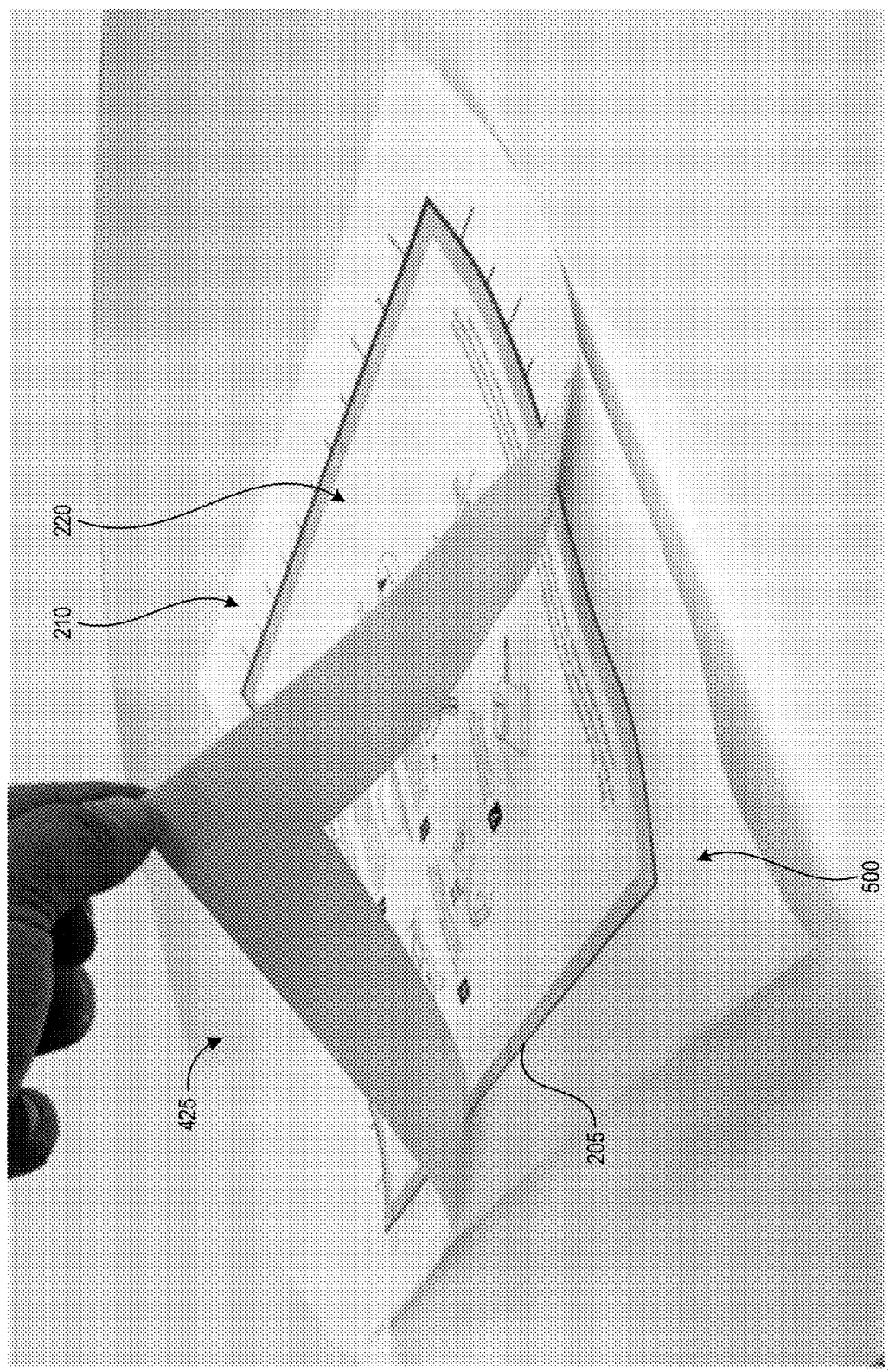

FIG. 4 illustrates example steps 400 of two different techniques for application of the template of FIGS. 2A-2C to a test surface. This can occur before or at step 102 of the process 100A described with reference to FIG. 1A above. Some embodiments of these techniques can be performed manually by a user, for example after the user puts on protective gloves at step 101 of the process 100A. Some embodiments can be performed using tools such as a roller that can help keep the user's hands away from the potentially contaminated test surface. For example, each individual template may be provided on a disposable roll. In another example, a reusable rolling tool can be provided with a number of templates. The templates can be connected end-to-end (e.g., via separation lines) along a rolled substrate, with the rolled substrate secured onto the reusable rolling tool such that multiple templates can be rolled onto desired surfaces from the reusable rolling tool. FIGS. 5A and 5B depict photographs of the template of FIGS. 2A-2C at different stages of the application process of FIG. 4, and so are discussed together with certain steps of FIG. 4 below.

Both techniques can begin at step 405, at which the user obtains the template, for example by removing the template from sterile packaging. Providing the disclosed templates in sterile packaging, such as heat sealed foil or polymer pouches, can assist in accurate measurements of test results by mitigating introduction of contaminants into the sample by the template. As described above, the template can be provided in two parts—a border and a removable central portion—both secured to a protective backing layer via adhesive.

For the first application technique (labeled a "corner rollout method"), the user moves to step 410 and peels off a corner of the template border from the protective backing. The corner peel indicator 216 described above can be positioned over this area of the border to guide the user in performing step 410. At step 410, the user can place the exposed adhesive at or around the corner onto the test surface to begin securing the template border to the surface. In some embodiments, the user may remove the removable portion 220 from the border prior to step 410, however in some embodiments the substrate of the removable portion can be flexible and it is not required to be removed. The user can bend the flexible protective backing, together with the removable portion if it remains secured to the protective backing, underneath the border (e.g., between the unsecured portion of the border and the test surface) and away from the secured corner of the border.

At step 415, the user can continue to roll the protective backing away from the secured corner as depicted by the arrow, thereby progressively peeling the protective backing off of the border. As additional portions of the adhesive of the border are exposed by this peeling, the user can press such portions onto the test surface, being careful to keep the interior edges of the border flat and straight to maintain the open area of the border at its expected size (e.g., by not wrinkling the border thus creating a smaller open area than expected for the template).

FIG. 5A depicts a photograph of an example of step 415 in which the removable portion 220 is still affixed to the protective backing layer. As shown in FIG. 5A, the user has bent the removable portion 220 under the unsecured portion of the border 210 and away from the secured corner (under graphic 216). The user pulls the backing layer and the removable portion 220 toward the corner that diagonally opposes the secured corner, thus peeling the backing from portions of the border 210. This peeling motion also separates the removable portion 220 from the border 210 along separation line 205, with separation line 205 now forming the interior edges of the border 210 that will demarcate the test area. The exposed adhesive is used to seal the border 210 to the test surface, with the user exercising care to keep the interior edges straight and to seal the corners such that the adjacent interior edges at the corner are positioned at 90 degrees to one another.

Once the backing has been completely removed from the border 210, the user adheres the final corner of the border 210 to the test surface, and the border 210 is fully adhered to the test surface as shown at step 420. The user can now proceed through the remaining sampling steps, for example moving to step 103 of the process 100A.

For the second application technique (labeled a "peel and place method"), the user moves from step 405 to step 425 to peel the template border away from the protective backing layer. FIG. 5B depicts a photograph of an example of step 425 in which the user is peeling the border 210 away from the protective backing layer 500. In this example, the removable portion 220 with the graphical use instructions is still secured to the backing layer 500. The user peeling the border 210 away from the protective backing layer 500 causes the border 210 to separate from the removable portion 220 along separation line 205, with separation line 205 now forming the interior edges of the border 210 that will demarcate the test area. In other embodiments the user may first remove the removable portion 220 from the interior of the border 210 before peeling the border 210 away from protective backing layer 500.

Once the border 210 has been completely removed from the protective backing layer 500, the user moves to step 430 to secure one edge of the border (in this example, the bottom edge) to the test surface. The user continues "rolling" the template onto the surface along two opposing edges that extend from the edge initially secured to the surface, gradually securing these edges to the surface and taking care to secure them parallel to one another and in straight lines. Once these two edges are secured to the test surface, the user finishes step 430 by securing the last edge to the test surface (in this example, the top edge), and the border 210 is fully adhered to the test surface as shown at step 420. The user can now proceed through the remaining sampling steps, for example moving to step 103 of the process 100A.

Implementing Systems and Terminology

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like. The phrase "based on" can mean "based only on" and "based at least on," unless expressly specified otherwise.

The previous description of the disclosed implementations is provided to enable any person skilled in the art to make or use the present disclosure. Various modifications to these implementations will be readily apparent to those skilled in the art, and the generic principles defined herein may be applied to other implementations without departing from the scope of the invention. Thus, the present invention is not intended to be limited to the implementations shown herein but is to be accorded the widest scope consistent with the principles and novel features disclosed herein.

What is claimed is:

1. A system for guiding collection of a hazardous contaminant sample, comprising:
   a handle configured for collection of the hazardous contaminant sample from a test surface, the handle comprising a swab configured to contact the test surface; and
   a template including
      a border having an outer perimeter and an inner perimeter with edges of the inner perimeter defining an open area configured to demarcate a test area for the collection of the hazardous contaminant sample,
      an adhesive configured for adhering at least the border to the test surface, and
      a plurality of alignment markings provided along at least one of the edges of the inner perimeter, the plurality of alignment markings provided at a spacing selected to provide visual guidance to a user for wiping the entire test area with the handle.

2. The system of claim 1, wherein the plurality of alignment markings are printed on a first surface of the border, the adhesive provided on a second surface of the border opposing the first surface.

3. The system of claim 2, further comprising a protective backing layer removably provided to cover the adhesive prior to use.

4. The system of claim 3, wherein the template further comprises a removable portion secured to the protective backing layer within the open area of the border.

5. The system of claim 4, the removable portion further comprising at least one graphical instruction for guiding the user through the collection of the hazardous contaminant sample printed on the first surface.

6. The system of claim 4, the system further comprising a separation line separating the border and the removable portion.

7. The system of claim 1, further comprising a reader device configured to determine a test result based on the hazardous contaminant sample collected from the test surface within the test area demarcated by the template.

8. The system of claim 7, wherein the border comprises a machine-readable pattern identifying the surface area of the test area, wherein the reader device includes:
   a scanning device,
   at least one computer-readable memory having stored thereon executable instructions, and
   one or more processors in communication with the at least one computer-readable memory and configured to execute the instructions to cause the reader device to
      cause the scanning device to capture data representing the machine-readable pattern, and
      determine the surface area of the test area based on analyzing the data.

9. A system for guiding collection of a hazardous contaminant sample, comprising:
   a template including a border having an outer perimeter and an inner perimeter with edges of the inner perimeter defining an open area configured to demarcate a test area for the collection of the hazardous contaminant sample; and
   a reader device configured to receive an indication of a surface area of the test area of the template, and to determine a test result based on the hazardous contaminant sample from the test surface and on the surface area of the test area of the template.

10. The system of claim 9, wherein the border comprises a plurality of alignment markings provided along at least one of the edges of the inner perimeter, the plurality of alignment markings provided at a spacing selected to provide visual guidance to a user for wiping the entire test area.

11. The system of claim 10, wherein the plurality of alignment markings are printed on a first surface of the border, the template further comprising an adhesive provided on a second surface of the border opposing the first surface.

12. The system of claim 11, further comprising a protective backing layer removably provided to cover the adhesive prior to use.

13. The system of claim 12, wherein the template further comprises a removable portion secured to the protective backing layer within the open area of the border.

14. The system of claim 13, the removable portion further comprising at least one graphical instruction for guiding the user through the collection of the hazardous contaminant sample printed on the first surface.

15. The system of claim 13, the system further comprising a separation line separating the border and the removable portion.

16. The system of claim 9, wherein one surface of the template is provided with an adhesive, the system further comprising a protective backing layer removably provided to cover the adhesive prior to use.

17. A template for guiding collection of a hazardous contaminant sample from a surface, comprising:
   a substrate comprising:
      a border having an outer perimeter and an inner perimeter with edges of the inner perimeter defining an open area configured to demarcate a test area on the surface for the collection of the hazardous contaminant sample,
      a separation line provided as one or more cuts through the substrate along the inner perimeter, and
      a removable portion provided within the inner perimeter;
   an adhesive provided on a surface of the substrate configured to secure at least the border to the surface; and
   a protective backing layer removably provided to cover the adhesive prior to use.

18. The template of claim 17, wherein the adhesive secures the border and the removable portion to the protective backing layer prior to use.

19. The template of claim 17, wherein the border comprises a plurality of alignment markings provided at a spacing selected to provide visual guidance to a user for wiping the entire test area.

20. The template of claim 17, wherein the removable portion comprises at least one graphical instruction for guiding a user through the collection of the hazardous contaminant sample.

21. The template of claim 17, wherein the removable portion is configured to be removed from the border prior to the collection of the hazardous contaminant sample.

22. A method for applying a template for guiding collection of a hazardous contaminant sample to a surface, comprising:
   obtaining the template of claim 17;

peeling the border away from the protective backing layer at a first corner of the border;

securing the first corner of the border to the surface using an exposed portion of the adhesive;

folding the protective backing layer away from the first corner and under a portion of the border that is unsecured to the surface;

peeling the protective backing layer away from the first corner to progressively expose more of the adhesive;

securing additional portions of the border to the surface using corresponding portions of the adhesive as it is progressively exposed; and upon fully removing the protective backing layer from the border, securing a second corner of the border to the surface, the second corner diagonally opposing the first corner.

23. A method for applying a template for guiding collection of a hazardous contaminant sample to a surface, comprising:

obtaining the template of claim 17;

completely removing the border from the protective backing layer;

securing a first edge of the border to the surface using a portion of the adhesive provided on the first edge;

progressively securing portions of second and third edges of the border onto the surface using corresponding portions of the adhesive provided on the portions of the second and third edges, the second and third edges extending from the first edge; and securing a fourth edge of the border to the surface using a portion of the adhesive provided on the fourth edge, the fourth edge opposing the first edge and connecting the second and third edges.

* * * * *